United States Patent
Trau et al.

(10) Patent No.: US 10,465,236 B2
(45) Date of Patent: Nov. 5, 2019

(54) NUCLEIC ACID DETECTION METHOD AND KIT

(71) Applicant: THE UNIVERSITY OF QUEENSLAND, Queensland (AU)

(72) Inventors: Matt Trau, St Lucia (AU); Eugene Wee, St Lucia (AU); Jose Ramon Botella, St Lucia (AU)

(73) Assignee: University of Queensland, Queensland (AU)

( * ) Notice: Subject to any disclaimer, the term of this patent is extended or adjusted under 35 U.S.C. 154(b) by 474 days.

(21) Appl. No.: 15/107,121

(22) PCT Filed: Dec. 23, 2014

(86) PCT No.: PCT/AU2014/050443
§ 371 (c)(1),
(2) Date: Jun. 22, 2016

(87) PCT Pub. No.: WO2015/095929
PCT Pub. Date: Jul. 2, 2015

(65) Prior Publication Data
US 2017/0029881 A1    Feb. 2, 2017

(30) Foreign Application Priority Data
Dec. 23, 2013  (AU) ................................ 2013905052

(51) Int. Cl.
| | |
|---|---|
| *C12P 19/34* | (2006.01) |
| *C12Q 1/6851* | (2018.01) |
| *C12Q 1/6844* | (2018.01) |
| *C12Q 1/689* | (2018.01) |
| *C12Q 1/6893* | (2018.01) |
| *C12Q 1/70* | (2006.01) |

(52) U.S. Cl.
CPC .......... *C12Q 1/6851* (2013.01); *C12Q 1/689* (2013.01); *C12Q 1/6844* (2013.01); *C12Q 1/6893* (2013.01); *C12Q 1/703* (2013.01); *C12Q 1/708* (2013.01)

(58) Field of Classification Search
CPC .......... C12Q 1/6844; C12Q 2527/119; C12Q 2563/143; C12Q 2563/149; C12Q 2565/113; C12Q 1/6851; C12Q 1/689; C12Q 1/6893; C12Q 1/703; C12Q 1/708
USPC ...................................................... 435/91.2
See application file for complete search history.

(56) References Cited

U.S. PATENT DOCUMENTS

| | | | |
|---|---|---|---|
| 6,096,563 A * | 8/2000 | Hajizadeh ........ | G01N 33/54313 435/7.1 |
| 2005/0059042 A1 | 3/2005 | Rothberg et al. | |
| 2012/0108451 A1 | 5/2012 | Li et al. | |
| 2013/0203045 A1 | 8/2013 | Landers et al. | |

FOREIGN PATENT DOCUMENTS

| | | |
|---|---|---|
| WO | WO 87/05334 | 9/1987 |
| WO | WO 97/03207 | 1/1997 |
| WO | WO 2003/035829 | 5/2003 |
| WO | WO 2012/009464 | 1/2012 |
| WO | WO 2012/151268 | 11/2012 |
| WO | WO 2014/065753 | 5/2014 |

OTHER PUBLICATIONS

Hawkins et al., Nucleic acids research, vol. 22, No. 21, pp. 4543-4544, (Year: 1994).*
CoreGenomics, http://core-genomics.blogspot.com/2012/04/how-do-spri-beads-work.html, pp. 1-3, 7 and 8, Jul. 3, (Year: 2013).*
Bailey et al., Clinical Chemistry, 56: 6, pp. 1022-1025, (Year: 2010).*
DeAngelis et al. (1995) Nucleic Acids Research 23(22):4742-4743 "Solid-phase reversible immobilization for the isolation of PCR products".
European Extended Search Report for 14873632.5 dated Jun. 6, 2017.
Li et al. (2013) Lab on a Chip 13:955-961 "Label-free DNA quantification via a 'pipette, aggregate and blot' (PAB) approach with magnetic silica particles on filter paper".
Wu et al. (2004) Journal of Microbiological Methods 56:395-400 "Detection of PCR amplicons from bacterial pathogens using microsphere agglutination".
Leslie et al. (2012) J. Am. Chem. Soc. 134:5689-5696 "New Detection Modality for Label-Free Quantification of DNA in Biological Samples via Superparamagnetic Bead Aggregation".

(Continued)

*Primary Examiner* — Cynthia B Wilder
(74) *Attorney, Agent, or Firm* — Adsero IP

(57) ABSTRACT

A method and kit for detecting a target nucleic acid is provided wherein combining an amplified nucleic acid with a particle such as a paramagnetic bead form a flocculated complex which can be detected by visual inspection. The volume of nucleic acid sample that can be detected is as low as a few microlitres. The method can be applied to in-the-field or point-of-care diagnosis for a rapid determination of the presence or absence of the target nucleic acid. The methylation status of a target nucleic acid can also be determined. The method and lit may have general applicability to detecting diseases in plants and animals, environmental testing and testing for contamination of foods and other edible products.

27 Claims, 9 Drawing Sheets

Specification includes a Sequence Listing.

(56) References Cited

OTHER PUBLICATIONS

Lin et al. (2013) Biosensors and Bioelectronics 47:515-519 "Naked-eye detection of nucleic acids through rolling circle amplification and magnetic particle mediated aggregation".
Smolensky et al. (2013) J. Am. Chem. Soc. 135:8966-8972 "Magnetoluminescent Light Switches—Duel Modality in DNA Detection".
Tan et al. (2005) Anal. Chem. 77:7984-7992 "Isothermal DNA Amplification Coupled with DNA Nanosphere-Based Colorimetric Detection".
International Search Report and Written Opinion of the International Searching Authority for PCT/AU2014/050443 dated Mar. 5, 2015.
Xia et al. (2010) PNAS 107(24):10837-10841 "Colorimetric detection of DNA, small molecules, proteins, and ions using unmodified gold nanoparticles and conjugated polyelectrolytes".

\* cited by examiner

SEQ ID NO. 29

NUCLEIC ACID DETECTION METHOD AND KIT

RELATED APPLICATIONS

This application is a 35 U.S.C. § 371 national phase application of PCT/AU2014/050443 (WO 2015/095929) filed on Dec. 23, 2014, entitled "Nucleic Acid Detection Method and Kit", which application claims the benefit of Australia Application Serial No. 2013905052, filed Dec. 23, 2013, all of which are incorporated herein by reference in their entirety.

SEQUENCE LISTING

Incorporated by reference herein in its entirety is the Sequence Listing entitled "28474US2_ST25.txt", created Jun. 21, 2016, size of 6 kilobytes.

FIELD

THIS INVENTION relates to nucleic acid detection. More particularly, this invention relates to rapid detection of nucleic acids using relatively small volumes of nucleic acid samples, where detection of the nucleic acid is by visual inspection.

BACKGROUND

Nucleic acid bioassays that can be performed on-site or at point-of-care (POC) with minimal equipment, rapidly and at low cost are in high demand. While there are many attempts aimed at achieving this, none are in practice currently. Techniques and methods for detecting disease DNA biomarkers are known, including the polymerase chain reaction (PCR) and ligase chain reaction (LCR)[1]. However, these methods require thermocycling on a thermal cycler to achieve rapid exponential DNA amplifications and hence are not suitable for field or on-site applications. Nonetheless, various isothermal DNA amplification methods have emerged recently to overcome this limitation[2,3]. For instance, to enable POC applications, pathogen DNA amplified by the recombinase polymerase amplification (RPA)[4] or helicase dependent amplification (HDA)[5] have been adapted for detection on lateral flow strips and portable fluorometers[6-9]. However, such readout methods whilst convenient, are still dependent on the use of relatively sophisticated equipment and may still present a financial obstacle for operators worldwide. Moreover, on-field sampling is rarely, if ever, discussed. In particular, consistently generating a fixed amount of sample DNA with minimal human manipulation and on-site infrastructure for downstream applications. This non-trivial issue may have significant impact on the performance of any assay. Therefore, a field-ready comprehensive assay for on-site nucleic acid detection applications is still an elusive aspiration.

One area that can benefit from low cost on-site assays is in agriculture. The agricultural industry is a major contributor to the world economy (estimated as $1500 billion per year). However, crop disease outbreaks are major issues in agriculturally reliant economies, especially in developing countries, with estimated yearly crop losses of $220 billion[10]. Currently, there is no way to salvage compromised crops once a disease outbreak spreads beyond a certain threshold. The ideal method to control disease outbreaks is by early detection in the field before it spreads. The effectiveness of crop disease management is highly dependent on the rapidness, sensitivity and specificity of the diagnostic method. Disease identification is traditionally done by visual examination of the disease phenotype in affected plant tissues. However this requires experienced plant pathologists and is relatively subjective[11]. Many sensitive diagnostic methods to enhance disease identification such as enzyme-linked immunosorbent assays (ELISAs)[12,13], immunoblots[14,15], immunofluorescent tests[16] and various iterations of PCR based assays[17,18] have been developed to facilitate disease diagnosis. However, all these detection methods require expensive and sophisticated equipment and can only be performed in laboratories by well-trained technicians. Moreover, the lack of rapid on-site detection can lead to delays in the deployment of disease control measures, which in turn, leads to further crop losses. It is therefore essential to develop new disease diagnostic technologies that can be applied in the field without the need to access specialized laboratory equipment. In addition, these technologies should be cheap, sensitive, reproducible and require no specialized personnel with the ultimate goal of allowing each farmer to monitor his or her own crops. Similarly, early detection of farm animal pathogens is essential to avoid the spread of diseases, especially in modern farms using intensive production methods. In addition, early diagnosis and detection of human diseases and the availability of POC methods nondependent on sophisticated technological requirements can save innumerable lives in developed as well as developing countries particularly after natural disaster situations such as typhoons, tsunamis or earthquakes.

SUMMARY

The inventors have realized the need for simple, reliable, rapid and inexpensive methods of nucleic acid detection. The invention therefore broadly provides a method and kit for rapid detection of nucleic acids in relatively small sample sizes, wherein the presence and/or absence of the nucleic acid can be visually detected. An advantage of the method is that in a preferred form, it obviates the need for equipment such as centrifuges, thermal cyclers and spectrophotometers, all of which require the availability of power in the form of mains electricity or batteries. In particular embodiments, the method or kit may be useful for detecting one or more non-pathogenic or pathogenic organisms of plants, human and non-human animals.

In a first aspect, the invention provides a method of detecting a nucleic acid, said method including the step of combining an isolated nucleic acid and a particle, wherein the isolated nucleic acid and the particle are capable of forming a complex which can be detected by visual inspection.

Suitably, the presence or relative amount of nucleic acid is indicated by the presence of, or a relatively increased level of visually-detectable complex compared to that observed in the absence of, or at a relatively lower amount or concentration of, the nucleic acid.

In one embodiment, the particle is a paramagnetic particle. In a preferred embodiment, the particle is an SPRI particle. Preferably, the particle forms a complex with the isolated nucleic acid at a pH<7. In a preferred embodiment, the pH is in the range of about 3.6-5.5 or more preferably about pH 4.4. According to this embodiment, the complex is formed by flocculation of the nucleic acid-particle complex.

In a further embodiment, the method may include use of a coloring agent to facilitate, assist or enhance visual detection of the nucleic acid-particle complex. Suitably, the coloring agent binds the nucleic acid and provides an optical signature at a wavelength in the visual range (i.e about 390 nm to about 700 nm). The optical signature may include absorption or emission of light (including phosphorescence and/or fluorescence) at a wavelength in the visual range.

Suitably, the isolated nucleic acid is obtained by nucleic acid sequence amplification of a template nucleic acid present in a nucleic acid sample. Typically, nucleic acid sequence amplification of the template nucleic acid includes one or more primers that are at least partly specific for the template nucleic acid. In a preferred form, the isolated nucleic acid is obtained by isothermal nucleic acid sequence amplification.

In one embodiment, isothermal nucleic acid sequence amplification is recombinase polymerase amplification (RPA).

In another embodiment, isothermal nucleic acid sequence amplification is rolling circle amplification (RCA).

Suitably, the template nucleic acid is present in a nucleic acid sample obtainable from any biological or other source of nucleic acid. In a preferred form, the template nucleic acid is obtained by one or more steps including: (a) gravity filtration of a nucleic acid sample that comprises the target nucleic acid; (b) binding of the target nucleic acid to a particle; and (c) elution of the target nucleic acid from the particle.

In typical embodiments, the volume of target nucleic acid at step (b) and/or at step (c) is about 10 µL.

In another aspect, the invention provides a kit for detecting a nucleic acid, said kit comprising a particle which is capable of forming a complex with an isolated nucleic acid, which complex is capable of being detected by visual inspection. The kit may further comprise one or more of: a nucleic acid polymerase for nucleic acid sequence amplification; one or more primers for nucleic acid sequence amplification; a magnet; reagents for nucleic acid extraction; a filter; a coloring agent; and/or one or more reaction vessels.

The method and/or kit may be used for the detection of nucleic acids of any origin, including humans and other animals, plants, pathogenic and non-pathogenic organisms inclusive of Protista, Archaea, bacteria, viruses, yeasts, fungi, worms and other invertebrate animals, although without limitation thereto.

In particular embodiments, the method and kit may be useful for detecting nucleic acids associated with diseases and conditions of humans, non-human animals and plants, environmental testing, testing of foods, beverages and other consumables and forensic analysis, although without limitation thereto.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE DRAWINGS

Non-limiting embodiments of the invention are described herein with reference to the following drawings.

(D) Whole blood methylation profiles of ESR1, GSTP1 and NYP from two prostate cancer samples (PC1 and PC2) and normal blood (NB) DNA pooled from 25 female donors. Top: Gel electrophoresis image of RPA reactions. Bottom: Photos showing flocculation as proxy for methylation states.

Figure 10:
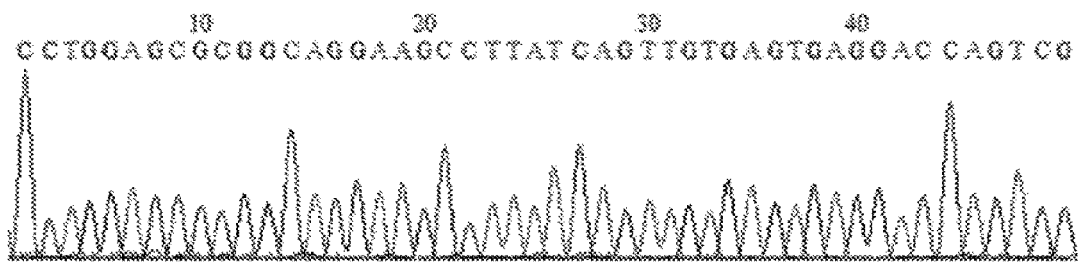

FIG. 10. DNA sequencing of DuCap RNA amplicons after RT-RPA. RT-RPA amplicons of extracted DuCap RNA was purified using SPRI magnetic beads and sequenced to verify amplification of target TMPRSS2:ERG region.

Figure 11:
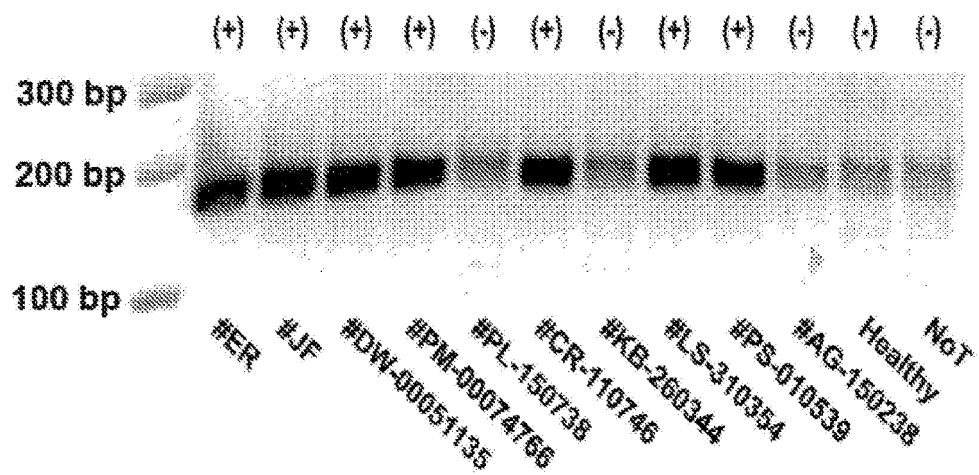

FIG. 11. RT-PCR of extracted RNA from patient urine specimens. Extracted RNA from urine specimens of 10 metastatic castrate-resistant prostate cancer patients and a healthy patient were amplified using RT-PCR for TMPRSS2:ERG detection. The RT-PCR amplicons were visualized on agarose gel and used to validate the screening results of our assay on the same group of patients (FIG. 11c).

Figure 12:
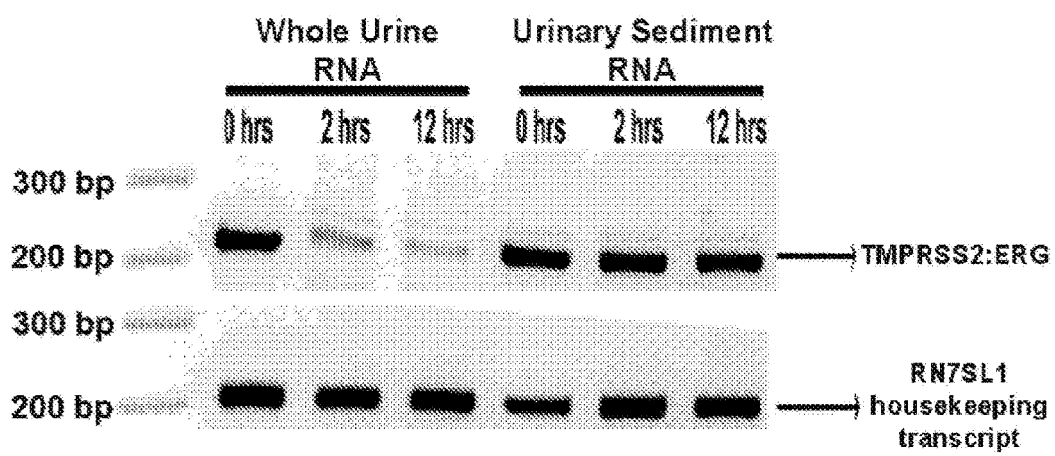

FIG. 12. Comparison of RNA stability in whole urine and urinary sediments. RT-RPA of patient whole urine and urinary sediment RNA extracted at 0, 2 and 12 hrs after specimen collection.

Figure 13:
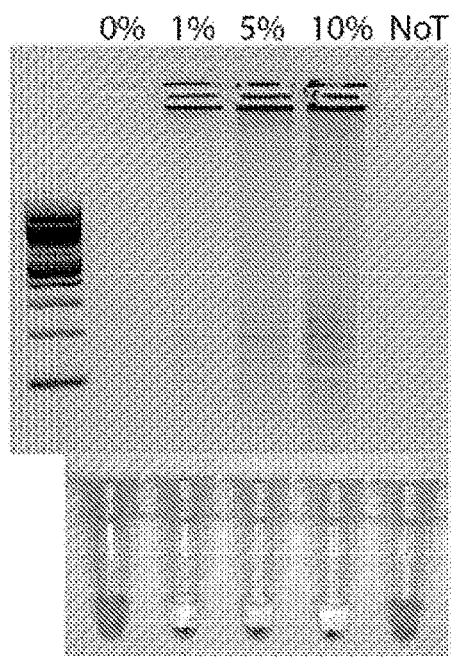

FIG. 13. Detection limit of RCA-SDG on different percentage of *Pseudomonas syringae* DNA (0%-10%) in *Arabidopsis thaliana* DNA with total input DNA of 5 ng. NoT: no template control. Top row: gel electrophoresis image corresponding RCA reactions performed. Bottom row: photographs of flocculation assay corresponding to the RCA reactions.

Figure 14:
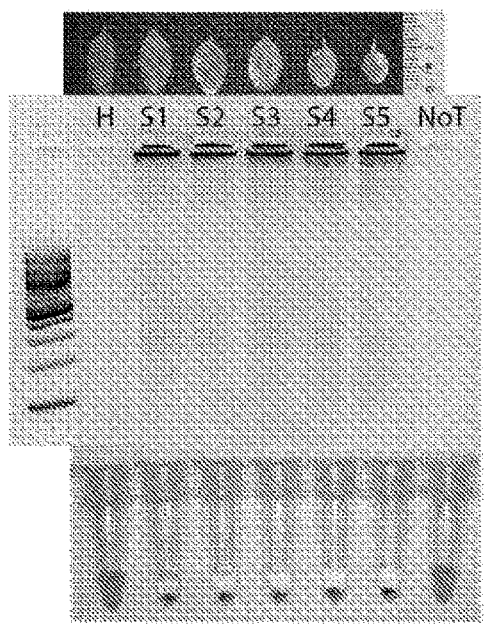

FIG. 14. Performance of Single Drop Genomic in the detection of *P. syringae* via RCA. Top row: photographs of leaves at various times after infection, S1 to S5. H: healthy sample. NoT: no template control. Middle row: gel electrophoresis images of corresponding RCA reactions performed on the same leaf. Bottom row: photographs of the flocculation assay corresponding to the RCA reactions.

DETAILED DESCRIPTION

The present invention relates to a method and kit for rapid, on-site detection of DNA in under 90 minutes. DNA sample sizes as low as 10 μL (i.e a single drop) can be used according to the invention. In a preferred form, solid phase reversible immobilization (SPRI) particles are used for precision sampling of nucleic acids that are purified to a precise concentration range, hence avoiding the need for further quantification in addition to ensuring optimal performance of downstream processes. Purified nucleic acids are then subject to any suitable nucleic acid sequence amplification system, such as isothermal nucleic acid sequence amplification, and then visualized with a DNA flocculation test using SPRI particles that flocculate the DNA under appropriate pH conditions. The inventors have demonstrated that the method could accurately detect various plant pathogens in *Arabidopsis thaliana* at various stages of infection. We were also able to distinguish between healthy and infected tissues in a commercial banana sample infected with an economically important pathogen. Finally, to demonstrate the versatility of this approach, the method has been used to detect a plant RNA virus in infected tissues, *E. coli*-laced water samples, HIV infected cells, malaria infected blood, influenza viruses in infected cells, Bovine herpesvirus 1 in bovine cells and *Mycobacterium tuberculosis* bacteria. Accordingly, the invention provides a method and kit that may be used to detect DNA from any source in a rapid manner with minimal equipment, thereby being ideally suited to point of care (POC) or other on-site applications, including providing a rapid response system for detecting new outbreaks of emerging diseases in human and non-human humans, animals and plants.

In an aspect, the invention provides a method of detecting a nucleic acid, said method including the step of combining an isolated nucleic acid and a particle, wherein the isolated nucleic acid and the particle are capable of forming a complex which can be detected by visual inspection.

In another aspect, the invention provides a kit for detecting a nucleic acid, said kit comprising a particle which is capable of forming a complex with an isolated nucleic acid, which complex is capable of being detected by visual inspection. The kit may further comprise one or more of; a nucleic acid polymerase for nucleic acid sequence amplification; one or more primers for nucleic acid sequence amplification; a magnet; reagents for nucleic acid extraction; a filter; and/or one or more reaction vessels.

Suitably, the kit may be used according to the method hereinbefore described. Accordingly, the kit may provide one or a plurality of polymerases, particles, buffers, vessels and other components that facilitate the preparation and visual detection of nucleic acids as disclosed herein.

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in native, chemical, synthetic or recombinant form.

The term "nucleic acid" as used herein designates single- and double-stranded DNA and RNA, including cDNA, genomic DNA, mRNA, RNA, cRNA, miRNA, tRNA, although without limitation thereto. A nucleic acid comprises a nucleotide sequence which typically includes nucleotides that comprise an A, G, C, T or U base. However, nucleotide sequences may include other bases such as inosine, methylcytosine, hydroxymethylcytosine, methylinosine, methyladenosine and/or thiouridine, although without limitation thereto.

As used herein, a "polynucleotide" is a nucleic acid having eighty (80) or more contiguous nucleotides, while an "oligonucleotide" has less than eighty (80) contiguous nucleotides. A "probe" may be a single or double-stranded oligonucleotide or polynucleotide, suitably labeled for the purpose of detecting complementary sequences in Northern or Southern blotting, for example. A "primer" is usually a single-stranded oligonucleotide, preferably having 15-50 contiguous nucleotides, which is capable of annealing to a complementary nucleic acid "template" and being extended in a template-dependent fashion by the action of a DNA polymerase such as Taq polymerase, RNA-dependent DNA polymerase or Sequenase™. A "template nucleic acid" is a nucleic acid subjected to nucleic acid amplification.

According to the invention, a nucleic acid sample may be obtained or extracted from any source inclusive of animals and plants, cells, tissues, fluids and sub-cellular organelles of animals and plants, bacteria, Archaea, Protista, fungi, viruses and environmental samples such as drinking water, effluents, swimming pool water, river or stream water, seawater etc and samples obtained from foods (e.g meat, dairy products etc) and other consumables. These sources may be in the form of pathology samples inclusive of body fluids (e.g cerebrospinnal fluid, blood, serum, plasma, semen, urine, lymph etc), tumour, tissue or organ biopsies, cervical samples and PAP smears, although without limitation thereto. Other sources include forensic samples that are suspected of containing detectable nucleic acids. Plant samples may be taken from leaves, stems, bark, seeds, fruit, flowers or flower components (e.g petals, anthers, pollen, stamen etc) roots and any other plant cells or tissues. The plant may be any member of the plant kingdom including crop plants such as cereals, legumes, sugarcane plants harvestable for flowers, nuts, seeds, oils, timber or fruit, plants grown for biomass such as algae, switchgrass, hemp and flax and any other plant of agronomic, aesthetic, ecological or commercial value. The animal may be any vertebrate or invertebrate animal, inclusive of fish, birds and mammals. In particular applications, the animal may be human, a non-human mammal or other animals of commercial value such as poultry, fish and crustaceans. Non-human mammals may include livestock (e.g. cattle, sheep, pigs, horses), domestic pets (e.g cats and dogs) and performance animals (e.g racehorses, camels), although without limitation thereto. Bacteria, Archaea, Protista, fungi and viruses may be pathogenic or non-pathogenic organisms. By "pathogenic" is meant that the organism is associated with, or causative of, a disease or condition of plants or animals. Non-limiting examples of pathogens may include viruses inclusive of RNA and DNA viruses, protozoa, fungi, worms inclusive of helminths, roundworms and annelids and bacteria inclusive of Gram +ve and Gram −ve bacteria.

Nucleic acid extraction may be by any method known in the art. Typically, nucleic acid extraction may be facilitated by extraction buffer which typically comprises a non-ionic detergent, salt, pH buffer and a chaotropic agent. Non-limiting examples of extraction buffers are provided in more detail hereinafter. Nucleic acids so obtained or extracted are referred to herein as a "nucleic acid sample". Typically, the nucleic acid sample is obtained by extraction from a source such as hereinbefore described, without subjecting the extracted nucleic acid to centrifugation or other significant g forces, or administration of non-atmospheric pressure (e.g. a vacuum) to facilitate removal of undesired particulate matter or debris. Preferably, the extracted nucleic acid is filtered under gravity or manually-generated pressure to facilitate removal of undesired particulate matter or debris. In a particularly preferred embodiment, the nucleic acid sample is at least partly purified using particles which reversibly bind a target nucleic acid in the nucleic acid sample, as will be described in more detail hereinafter. Suitably, the target nucleic acid may subsequently be amplified by a nucleic acid amplification technique.

Nucleic acid amplification techniques are well known to the skilled addressee, and include but are not limited to polymerase chain reaction (PCR); strand displacement amplification (SDA); rolling circle amplification (RCA); nucleic acid sequence-based amplification (NASBA), Q-β replicase amplification; helicase-dependent amplification (HAD); loop-mediated isothermal amplification (LAMP); nicking enzyme amplification reaction (NEAR) and recombinase polymerase amplification (RPA), although without limitation thereto. As generally used herein, an "amplification product" refers to a nucleic acid product generated by a nucleic acid amplification technique.

Many nucleic acid amplification techniques cycle the nucleic acid sequence amplification procedure through different temperatures (e.g 95° C. for denaturation, 72° C. for primer annealing and 42° C. for template extension) during each round of amplification, thereby requiring a thermal cycler for the technique. However, some nucleic acid amplification techniques may be isothermal, such as SDA, LAMP, NEAR, HAD, RCA and RPA, thereby obviating the need for a thermal cycler. Accordingly, in a preferred embodiment the method and kit utilizes isothermal nucleic acid sequence amplification. A particular embodiment of isothermal nucleic acid sequence amplification is RPA, such as provided by the TWISTDX™ system, although without limitation thereto. Table 1 provides non-limiting examples of primers that are useful for isothermal nucleic acid amplification by RPA. Another particular embodiment of isothermal nucleic acid sequence amplification is RCA, which will be described in more detail in the following Examples.

However, it will also be appreciated that in a less preferred embodiment, nucleic acid amplification may be performed using a thermal cycler or otherwise by a method that includes repeated cycles of nucleic acid sequence amplification through different temperatures during each round of amplification.

Suitably, the amplification product is subsequently immobilized and then visualized by formation of complex with a particle. In a further embodiment, a coloring agent may be used to facilitate, assist or enhance visual detection of the nucleic acid-particle complex. Suitably, the coloring agent binds the nucleic acid and provides an optical signature at a wavelength preferably in the visual range (i.e about 390 nm to about 700 nm). The optical signature may include absorption or emission of light (including phosphorescence and/or fluorescence) at a wavelength in the visual range.

It will be appreciated from the foregoing that the method and kit utilize a particle that is capable of binding a nucleic acid such as DNA, preferably double-stranded DNA (dsDNA). The particle is capable of binding the template nucleic acid after preparation of the nucleic acid sample and/or is capable of forming a complex with an isolated nucleic acid that can be detected by visual inspection.

In the general context of the present invention, a "particle" may be any matrix, bead or substrate capable of binding to an isolated nucleic acid. In a preferred form, the particle selectively binds an isolated nucleic acid having at least 100 contiguous nucleotides. This property facilitates selection of an amplification product having at least 100 contiguous nucleotides from nucleic sequence amplification primers (which are typically much shorter than 100 contiguous nucleotides) and any shorter, incomplete, non-specific or truncated amplification products. Suitably, the particle comprises a charged surface which facilitates binding or interacting with the isolated nucleic acid. Preferably, the charges surface comprises positive charge which facilitates binding or interacting with a negatively charged isolated nucleic acid.

In some embodiments, the particles may be paramagnetic beads. Typically, paramagnetic beads comprise a polymer core (e.g. polystyrene), a paramagnetic shell (e.g magnetite or other iron-containing paramagnetic materials such as clays including montmorillonite and nontronite, biotite, siderite, pyrite) and a coating that comprises one or more chemical moieties that bind nucleic acids under appropriate conditions (e.g carboxyl-containing moieties). Non-limiting examples include SPRI particles and AMPUREXP™ SPRI particles. A preferred paramagnetic particle is an SPRI particle.

In other embodiments, particles may include metal particles such as gold (e.g DNADEL™ Gold Carrier Particles), metal hydroxides such as hydrotalcite (HT) and hydroxyapatite (HA), silicates such as diatomaceous earth, although without limitation thereto.

In the context of binding the template nucleic acid after preparation of the nucleic acid sample, suitably the particle is capable of reversibly binding the nucleic acid. Accordingly, under suitable conditions the particle binds the nucleic acid, which nucleic acid may then be eluted or otherwise released from the particle under conditions which facilitate elution or release of the nucleic acid. Preferably, an amount or concentration of particles is provided whereby a consistent, reproducible amount or concentration of nucleic acid is bound and eluted.

One non-limiting example of a particle that is capable of reversibly binding a template nucleic acid is an SPRI particle, as hereinbefore described.

In the context of particles binding a nucleic acid, such as a dsDNA amplification product following nucleic acid sequence amplification, suitably the formation of a nucleic acid: particle complex can be detected, observed or measured by visual inspection. By this is meant that a human observer with substantially unaided vision can see at least the presence or absence of a complex formed between the particle and the nucleic acid. Visual detection may provide a qualitative, semi-quantitative or quantitative measurement of the nucleic acid: particle complex. A semi-quantitative or quantitative determination or measurement by visual inspection may provide at least an approximate amount or concentration of the complex formed between the particle and the nucleic acid. By way of example, quantitation may be determined with reference to titrated reference standards which comprise different amounts or concentrations of nucleic acid:particle complexes. One non-limiting example of a particle that is capable of forming a complex with dsDNA that can be detected by visual inspection is an SPRI particle, as hereinbefore described. According to this example, nucleic acid:SPRI particle complexes are visualized as flocculated complexes. Typically, a relatively clear or colourless solution upon treatment with a magnet is formed as a result of the flocculated complex being readily attracted by the magnet. This is in contrast to an absence of nucleic acid: SPRI particle complexes which results in a coloured or turbid solution. The relative clarity or lack of colour may be a measure of the amount or concentration of the nucleic acid, such as when titrated against known amounts or concentrations of nucleic acid. A preferred method would be to titrate pH until a flocculate is reduced or absent and the amount of base added is an approximation or estimate of the amount of nucleic acid.

However, it should also be appreciated that the method does not exclude the use of apparatus, devices or equipment which assists detecting, observing or measuring formation of the nucleic acid: particle complex. Non-limiting examples of apparatus, devices or equipment include nephelometers, turbidometers and spectrophotometers, although without limitation thereto.

In some embodiments, the particle binds a nucleic acid in a manner that is not nucleotide sequence-specific. Essentially, the particle binds the nucleic acid (e.g a nucleic acid amplification product) by virtue of a physicochemical interaction with the nucleic acid. By way of example, this may include an electrostatic or charge interaction between a negatively charged nucleic acid and a negatively charged particle, such as assisted by way of the carboxyl-containing moieties coating an SPRI particle. Positively charged particles such as, but not limited to, amine-containing moieties coated particles may also be used.

In other embodiments, the particle binds the nucleic acid in a manner that is nucleotide sequence-specific. By way of example, the particle may be coupled to an oligonucleotide probe that comprises a nucleotide sequence capable of hybridizing to a nucleic acid amplification product. This nucleotide sequence-specific detection may be capable of discriminating nucleotide sequence polymorphisms, such as different allelic forms, SNPs and other nucleotide sequence variants of interest, such as those associated with particular plant or animal diseases.

In the context of the aforementioned general embodiments, a particular embodiment of the method includes the steps of:

(a) obtaining a nucleic acid sample;
(b) subjecting the nucleic acid sample to isothermal nucleic acid sequence amplification to thereby produce a nucleic acid amplification product from a template nucleic acid, if present in the nucleic acid sample; and
(c) combining the nucleic acid amplification product and a paramagnetic particle, wherein the isolated nucleic acid and the particle are capable of forming a complex which is capable of being detected by visual inspection.

In step (a), it is preferred that the nucleic acid sample is obtained by extraction from a source such as hereinbefore described, without subjecting the nucleic acid sample to centrifugation or other significant g forces, under vacuum or high pressure, (the sample may be subjected to low pressure such as by way of a manually-operated syringe) to facilitate removal of undesired particulate matter or debris. Suitably, the nucleic acid sample is filtered under gravity to thereby remove undesired particulate matter or debris. In some embodiments, the filter is a micropipette tip or other conduit (e.g a glass pipette, cannula or tubing) at least partly filled with a filter material such as cotton wool. Subsequently, the nucleic acid sample is combined with paramagnetic particles such as SPRI particles in a suitable buffer to thereby form a complex between the nucleic acid and the paramagnetic particles. Typically, although not exclusively, the buffer comprises polyethylene glycol, salt and a pH buffer. Typically, the volume of nucleic acid sample combined with the paramagnetic particles is substantially less than the volume of the nucleic acid sample obtained by extraction from the source. The volume of nucleic acid sample combined with the paramagnetic particles may be no more than 20%, no more than 10%, no more than 5%, or no more than 4%, 3%, 2% or 1% of the volume of the nucleic acid sample obtained by extraction from the source. Suitably, the volume may be no more than about 50 µL, no more than about 40 µL no more than about 30 µL, no more than about 20 µL or no more than about 5-10 µL, inclusive of 5 µL, 6 µL, 7 µL, 8 µL and 9 µL.

Suitably, the complex is subsequently immobilized by a magnet, the buffer removed and the nucleic acid is eluted from the particles. Elution may be achieved using an eluent such as water, although without limitation thereto. Suitably, the eluted volume may be less but no more than about 50 µL, no more than about 20 µL, or no more than about 5-10 µL inclusive of 5 µL, 6 µL, 7 µL, 8 µL and 9 µL. The amount, concentration, ratio or relative proportion of paramagnetic particles combined with the nucleic acid sample is optimally determined so that a desired amount or concentration of nucleic acid is eluted from the paramagnetic particles. For example, a desired yield may be 3-5 ng/µL of high molecular weight DNA in a 10 µL elution.

In step (b), it is preferred that the isothermal nucleic acid sequence amplification is by RPA, preferably performed at about 37° C. although without limitation thereto. In step (b) primers are utilized that provide specificity for the target nucleic acid in the nucleic acid sample, whereby the target nucleic acid is preferentially amplified, if present in the nucleic acid sample. Non-limiting examples of primers are described in Table 1.

In step (c) the amplification product produced at step (b) is combined with paramagnetic particles, such as SPRI particles. Typically, the amplification product is combined with the paramagnetic particles in a flocculation buffer that facilitates the formation of a complex between the paramagnetic particles and the amplification product that can be visually detected. The flocculation buffer suitably has a pH below 7. Preferably, the pH is in the range 3-6 or more preferably in the range of about pH 3.6-5.5, inclusive of pH 3.7, 3.8, 3.9, 4.0, 4.1, 4.2, 4.3, 4.4, 4.5, 4.6, 4.7, 4.8, 4.9, 5.0, 5.1, 5.2, 5.3 and 5.4, or any range between these stated pH values. As described hereinafter, a non-limiting example is pH 4.4. By way of example, the flocculation buffer may be or may comprise one or more acetate, citrate, phosphate or dihydrogen phosphate salts, although without limitation thereto. As described in more detail hereinafter, a non-limiting example of a flocculation buffer is a sodium acetate buffer pH 4.4.

Although not wishing to be bound by any particular theory, it is proposed that nucleic acid:particle flocculation may be reversible by increasing the flocculation buffer pH, which is consistent with flocculation being a reversible non-covalent aggregation of colloids. Accordingly, at higher pH, nucleic acids such as DNA are more negatively charged and hence is more likely to repel other negatively charged nucleic acids from the carboxylic acid coated surface of the particle (e.g. an SPRI particle). This pH dependence may be exploited to fine-tune the sensitivity of the method according to nucleic acid concentration. Post-flocculation titration of pH may also be used as an approximation or estimation of nucleic acid concentration.

As previously described, a coloring agent may be used to facilitate, assist or enhance visual detection of the nucleic acid-particle complex. Suitably, the coloring agent binds the nucleic acid and provides an optical signature at a wavelength in the visual range (i.e about 390 nm to about 700 nm). The optical signature may include or result from absorption or emission of light (including phosphorescence and/or fluorescence) at a wavelength in the visual range.

Such coloring agents may be typically known as "DNA dyes", non-limiting examples being crystal violet, a crystal violet/methyl orange mixture, methylene blue or VISUAL VIOLET™ (i.e., crystal violet).

The method and kit of the present invention provides a "platform" technology that may have numerous applications in the field of nucleic acid detection. More particularly, the method and kit of the present invention provides a sensitive and cost-effective means for detecting nucleic acids in the field or at the "point of care". In a preferred form, the present invention at least minimizes or entirely obviates the need for equipment such as thermal cyclers, centrifuges, spectrophotometers and the like. By way of example, the present invention may have utility in the detection of plant and animal disease pathogens, the detection of a genetic predisposition of a plant or animal to a particular inherited trait or disease, the analysis of foods and other consumables to detect spoilage by fungal or bacterial contamination, water quality monitoring, analysis of forensic samples, preimplantation genetic analysis, sex determination and DNA fingerprinting, although without limitation thereto.

Particular embodiments of the invention relate to the detection of plant or animal disease pathogen.

In this context, a particular embodiment of the method includes the steps of:
(I) obtaining a nucleic acid sample from a plant or animal source;
(II) subjecting the nucleic acid sample to isothermal nucleic acid sequence amplification to produce a nucleic acid amplification product from a template nucleic acid if present in the sample, wherein the template nucleic acid comprises a nucleotide sequence which is of a pathogen that is causative of, or associated with, a disease or condition of the plant or animal; and
(III) combining the nucleic acid amplification product, if present, with paramagnetic particles, wherein the nucleic acid amplification product and the particle are capable of forming a complex which can be detected by visual inspection, wherein the presence of the nucleic acid amplification product indicates the presence of the pathogen.

Therefore, in some embodiments the present invention may be used for medical or veterinary diagnostics to determine the presence of absence of a pathogen that is associated with, or causative of a disease or condition of the animal. In this context, animals may include human and non-human mammals (e.g livestock and pets), fish, crustaceans and avians (e.g poultry), although without limitation thereto Pathogens may include viruses inclusive of RNA and DNA viruses, protozoa, worms inclusive of helminths, roundworms and annelids, fungi, Protista, Archaea and bacteria. As will be described in more detail in the Examples, the method detected nucleic acids of pathogens of human diseases caused by viruses such as HIV and influenza, protozoa such as *Plasmodium falciparum* and bacteria such as *E. coli* and *Mycobacterium tuberculosis*.

Detection of fungal, viral and/or bacterial plant pathogens is also contemplated according to the invention. Plants may include monocotyledonous and dicotyledonous plants, crops, cereals, fruits, grasses, trees & vines, although without limitation thereto. Non-limiting examples of plant pathogens include DNA and RNA viruses such the RNA virus cucumber mosaic virus, bacteria such as *Pseudomonas syringae* and fungi such as *F. oxysporum* f.sp. *conglutinans* and *Botrytis cinerea* as described in more detail in the Examples.

However, it will be appreciated that the invention may be broadly practised using nucleic acid samples obtainable from any organism, whether a non-pathogenic organism or a pathogen of human and non-human animals or plants.

One particular application of the present invention is in relation to new disease outbreaks in human or animal populations or in plant populations such as crops. As has recently occurred with avian influenza and other influenzas and also SARS, new pathogen strains or variants emerge which are genetically distinguishable. The genomes of such new pathogen strains or variants may be rapidly sequenced and nucleic acid sequence amplification primers generated which are suitable for use according to the present invention. The method and kit of the invention is thereby immediately adaptable for use with the nucleic acid sequence amplification primers to provide rapid and simple detection of the new pathogen strains or variants.

Other particular embodiments of the invention relate to the detection of biomarkers associated with a particular disease or condition.

In this context, a particular embodiment of the method includes the steps of:
(I) obtaining a nucleic acid sample from a human or non-human animal;
(II) subjecting the nucleic acid sample to isothermal nucleic acid sequence amplification to produce a nucleic acid amplification product from a template nucleic acid if present in the sample, wherein the template nucleic acid comprises a nucleotide sequence that is, or encodes a biomarker associated with a disease or condition; and (III) combining the nucleic acid amplification product, if present, with paramagnetic particles, wherein the nucleic acid amplification product and the particle are capable of forming a complex which can be detected by visual inspection, wherein the presence of the nucleic acid amplification product indicates the presence of the biomarker.

The biomarker may be associated with any disease or condition of human or non-human animals, inclusive of cancers, tumours, lymphomas, leukaemias and other malignancies, infectious diseases, inflammatory diseases, autoimmune diseases, respiratory diseases, gastrointestinal diseases, neural diseases, diseases of the reproductive system and psychiatric conditions, although without limitation thereto. For example, the biomarker may be or include a tumour antigens, suppressor genes or markers and/or genetic or epigenetic nucleotide sequence polymorphisms, mutations modifications or changes such as somatic mutations, single nucleotide polymorphisms (SNPs) and other inherited polymorphisms, nucleotide sequence insertions, deletions, rearrangements, DNA methylation and/or DNA hydroxymethylation events, although without limitation thereto. In one particular embodiment described in more detail in the Examples, the method and/or kit disclosed herein is suitable for detecting DNA methylation. In another particular embodiment described in more detail in the Examples, the method and/or kit disclosed herein is suitable for detecting a DNA marker of prostate cancer.

Further particular embodiments of the invention relate to the detection of pathogens in environmental samples.

In this context, a particular embodiment of the method includes the steps of:
(1) obtaining a nucleic acid sample from an environmental source;
(2) subjecting the nucleic acid sample to isothermal nucleic acid sequence amplification to produce a nucleic acid amplification product from a template nucleic acid, if present in the sample, wherein the template nucleic acid comprises a nucleotide sequence of a pathogen; and
(3) combining the nucleic acid amplification product, if present, with paramagnetic particles, wherein the nucleic acid amplification product and the particle are capable of forming a complex which can be detected by visual inspection, wherein the presence of the nucleic acid amplification product indicates the presence of the pathogen.

The environmental source or sample may be water inclusive of waste water and effluent (e.g sewerage, storm water, mining and/or industrial waste-water), drinking water, swimming pool water and river, creek, lake, pond or seawater, air samples and soil samples, although without limitation thereto.

So that the invention may be readily practised and put into practical effect, reference is made to the following non-limiting Examples.

EXAMPLES

Example 1

Single Drop Genomics

Materials & Methods

For plant applications, genomic DNA was extracted from a single leaf (300 mg) using an optimized lysis buffer (50 mM Tris-HCl pH 8.0, 1.5 M guanidium-HCl, 2% w/v PVP40 and 1% v/v Triton-X). For DNA applications, 400 ng/µL RNase A was added to the lysis buffer but not for RNA applications. After a 10 min incubation at ambient conditions, the lysate was cleared using a low cost homemade filtration device made from a common filtered pipette tip. For non-plant applications, lysis buffer without PVP40 was used. Nucleic acids were then purified using a modified SPRI protocol.[19,20] Briefly, a single drop (10 µL) of the cleared lysate was incubated with 1.8 volumes of carboxylic acid coated magnetic beads (Thermo Fisher) in a binding buffer (10 mM Tris-HCl pH 8.0, 20% PEG8000, 2.5 M NaCl) for 5 mins DNA bound beads were then separated from the lysate with a magnet and washed twice with 100% isopropanol, followed by two 80% ethanol washes and eluted in 10 µL of water.

The TwistAmp Basic RPA Kit (TWISTDX) was used as recommended by the manufacturer with some modifications. Briefly 12.5 µL reactions were performed at 37° C. for 30-40 mins using 1 µL, of the nucleic acid extraction and 480-600 nM of each primer (Table 1). For RNA applications, 50 units of MMuLV reverse transcriptase were added to the RPA reaction. Following amplification, 5 µL of the RPA reaction was electrophoresed on gel to verify amplification. Another 5 µL was used in the flocculation assay by incubating 5 min with 1.8 volumes of magnetic SPRI bead solution. After bead separation with a magnet and an 80% ethanol wash, 30 µL of flocculation buffer (100 mM sodium acetate, pH 4.4) was added to the beads.

Results

Single Drop Genomics Concept

Figure 1:
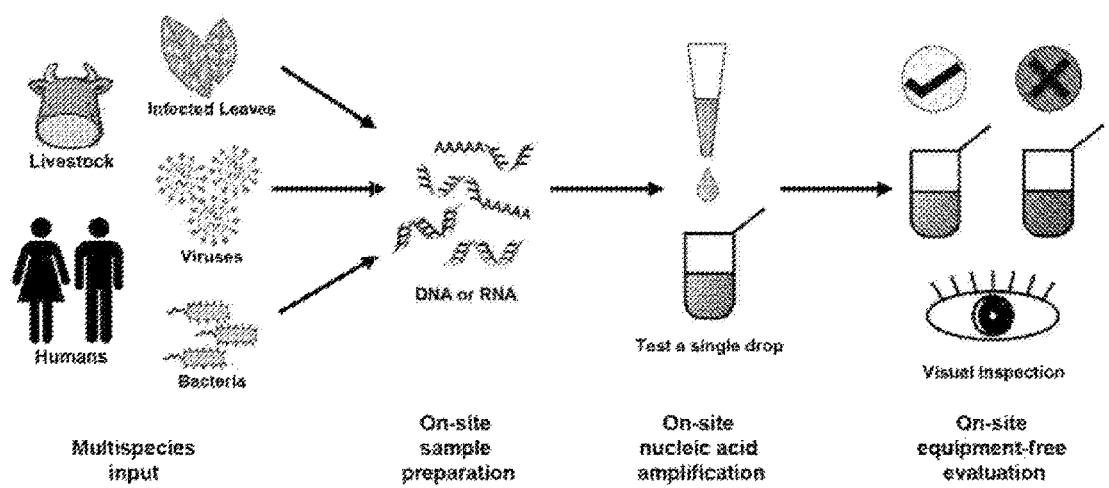
FIG. 1. Schematic of the Single Drop Genomics assay. A sample of interest is processed on-site by a simple nucleic acid extraction approach to a narrow concentration range. Pathogen nucleic acids are then detected and amplified isothermally by Recombinase Polymerase Amplification. Finally, assay results are visualized by a novel flocculation assay.

Single Drop Genomics was conceived as a comprehensive integrated solution for on-site sensitive and rapid detection of pathogenic nucleic acids with minimal equipment. FIG. 1 briefly describes the SDG concept which consists of three main phases. The first phase is precision sampling where DNA and/or RNA is extracted to a narrow concentration range using minimal equipment from a source of interest, e.g. a single drop of crude leaf extract. The second phase is the sensitive, rapid isothermal amplification of pathogenic nucleic acids using RPA. The third and final phase is the specific capture of amplified DNA using SPRI followed by a virtually equipment-free visual inspection of the same SPRI particles in a flocculation inducing buffer.

Precision DNA Sampling

On field sampling is rarely, if ever, discussed. This non-trivial task of consistently generating a fixed amount of sample has significance on the performance of any assay. Here, we describe a low cost DNA purification using common filtered pipette tips in conjunction with SPRI technology[19] to consistently extract DNA to a precise concentration that could be used immediately for downstream RPA amplification (FIG. 2A). Magnetic SPRI bead-based DNA extractions are ideal for POC applications because it is virtually equipment-free; requiring only a magnet. Moreover, DNA yield can be precisely controlled simply by adjusting the amount of SPRI particles given a fixed sample input. Another advantage of this approach is its relatively low cost (approximately 10 Australian cents per extraction). After manual maceration of a single leaf (approximately 300 mg or four 6 mm diameter discs) with a plastic mortar in 200 µL of lysis buffer, plant lysate was cleared of cellular debris by simply passing the lysate through a filtered pipette tip. DNA was then purified using SPRI from a single drop (10 µL) of lysate which resulted in consistent typical yields of 3-5 ng/µL of high molecular weight DNA in a 10 µL elution. As DNA yield was near to the detection limit for spectrometric evaluation (Nanodrop), DNA yield and integrity was estimated by ethidium bromide staining (FIG. 1B) and validated using fluorescence (Qubit® assay). Although DNA evaluation was not possible with spectrometry, near baseline absorbance at 230 nm indicated minimal amounts of contaminants (FIG. 2C). For RNA extractions, typical yields were 30-40 ng/μL in a 10 μL elution with 260/280 and 260/230 ratios of 1.9-2.2 and 1.8-2.3 respectively (FIG. 2C), indicating good purity.

DNA Flocculation Assay

Aggregation assays have several benefits such as label-free and equipment-free biomolecule detection and have been demonstrated more recently with gold nanoparticles[21-23]. Herein, to the best of our knowledge, we demonstrate for the first time, a flocculation assay using SPRI carboxylic acid coated magnetic particles for DNA detection (FIG. 3A). The use of magnetic SPRI particles has three benefits: (1) to bind RPA amplified DNA, (2) to remove excess dNTPs, primers and primer dimers, (3) to facilitate a buffer change for flocculation. As the current SPRI condition excludes DNA less than 100 bp[19], excess primers up to 600 nM (the maximum primer concentration recommended for RPA) did not result in agglutination (FIG. 3B). However, agglutination (positive response) occurred only in the presence of amplified DNA (FIG. 3C). In addition, as little as 10% amplification efficiency was needed to illicit a visually distinct positive response. This was estimated by assuming that the maximum amount of amplified products was the same as the initial amount of primers (480 nM) in the reaction. Various proportions of product to primers were then mixed to determine the minimum amplification needed to induce flocculation. Another interesting feature of the assay was its sensitivity to pH changes (FIG. 3D). At pH 4.4, as little as 0.5 ng/μL (5 μL volume) of amplified product could be detected. However, at pH 5.4, the cutoff concentration for agglutination increased 100-fold to 50 ng/μL (5 μL volume). Thus, this feature could offer some level of "tuning" and may be beneficial for certain applications. Considering these observations, we concluded that the mechanism causing the agglutination was likely DNA mediated flocculation of the SPRI particles.[24]

Figure 4:
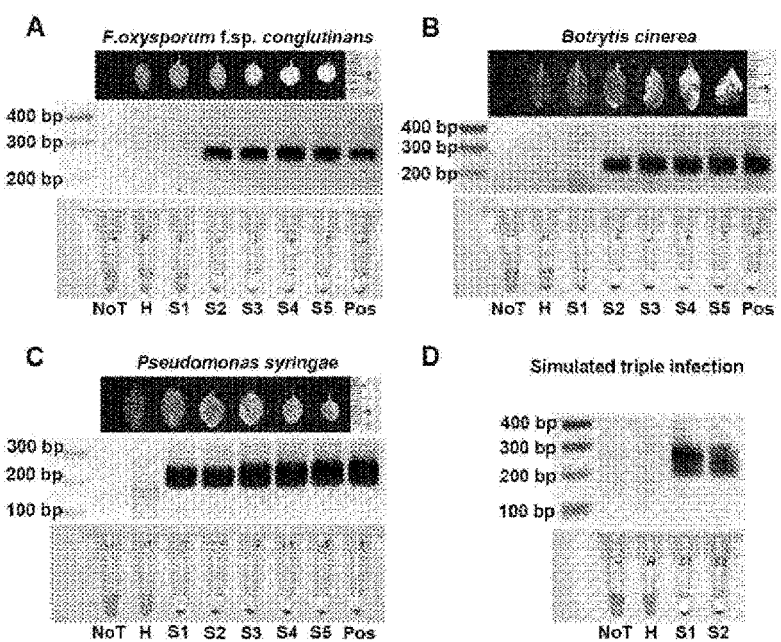
FIG. 4. Performance of Single Drop Genomics in detecting three plant pathogens. (A) *Fusarium oxysporum* f.sp. *conglutinans*, (B) *Botrytis cinerea*, (C) *Pseudomonas syringae*, (D) simulated triple infection. Top row: photographs of leaves at various stages of infection S1 to S5. H: healthy sample. Pos: positive control. NoT: no template control. Middle row: gel electrophoresis images of corresponding RPA reactions performed on the same leaf. Bottom row: photographs of the flocculation assay corresponding to the RPA reactions.
Figure 5:
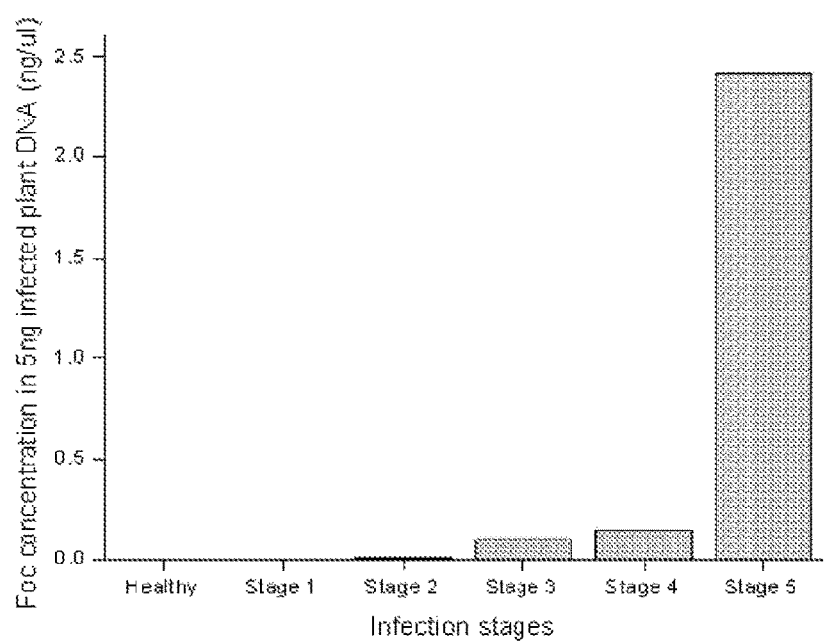
FIG. 5. qPCR quantification of *F. oxysporum conglutinans* (FOC) in 5 ng of DNA extracted from leaves at various stages of infection. Pathogen DNA was detectable from stage 3 infection onwards using the same primers used for RPA in FIG. 4.

Detecting Plant Pathogens at Various Stages of Infection Using Single-Drop Genomics We chose to demonstrate the feasibility SDG by detecting plant pathogens because crop loss due to late disease diagnosis is a significant problem[10]. Moreover, on-field assays for agricultural applications are currently lacking. Using our precision sampling procedure, DNA was collected from pathogen-inoculated *Arabidopsis thaliana* at various stages of infection based on their symptom development. Using SDG, as early as stage one infection could be detected for *Pseudomonas syringae* inoculated plants even before symptoms manifested (FIG. 4C). In addition, SDG detected *F. oxysporum* f.sp. *conglutinans* and *Botrytis cinerea* in inoculated plants from stage two of infection when symptoms started becoming apparent (FIG. 4A & FIG. 4B). We also attempted to verify our SDG results for *F. oxysporum* f.sp. *conglutinans* using qPCR, however, with the same amount of starting material as the RPA approach, only stage 3 to 5 could be detected with (FIG. 5). To demonstrate a triplex detection assay, leaves from three plants inoculated with different pathogens were pooled together at their respective stages of infection to simulate a triple infection. SDG could detect the presence of pathogens at stage one (FIG. 4D). These results not only demonstrate the feasibility of the SDG assay but also the sensitivity in early detection of plant infections i.e. when phenotypic symptoms just begin to manifest.

While SDG performs well in the *Arabidopsis thaliana* plant model system, we wondered if the assay could be applicable on other host plant systems. To this end, we applied SDG on banana stem cuttings (from a commercially important variety) to detect *F. oxysporum cubense*. SDG was readily able to distinguish a healthy from a diseased sample, further supporting SDG's potential as a viable on-site field test for agricultural applications (FIG. 6A).

Single-Drop Genomics: Multispecies Application

While we have successfully detected plant pathogen DNA, detecting RNA may also be useful for RNA viruses. To this end, the SDG sampling protocol was modified to extract RNA instead of DNA for the plant pathogen cucumber mosaic virus (CMV). MMLV reverse transcriptase (RT) was then added to the RPA mix to allow for an isothermal, single-step RT-RPA amplification of viral RNA.[25,26] Successful amplification was then determined with the flocculation assay and verified by gel electrophoresis. As expected, only samples with viral infection but not healthy plants yielded a positive result when RT enzyme was included in the RPA reaction (FIG. 6E).

To demonstrate other potential agricultural applications, we turned our attention to the cattle industry. Cattle farms tend to be located in geographically remote areas. Hence, an on-site diagnostic for cattle disease such as the bovine herpesvirus 1 could benefit the industry. Infected and uninfected bovine cells were subjected to SDG and we successfully distinguished between healthy and diseased samples using primers against the viral tyrosine kinase 1 and glycoprotein B genes (FIG. 6F).

SDG was next used to detect *E. coli* DNA in water. The common laboratory *E. coli* strain OneShot Mach1 was cultured until an OD=0.5. This was then diluted 10 fold and 10 μL was used for DNA extraction. 1 μL of the extracted DNA was then used in the amplification step with primers targeting an *E. coli* specific sequence in the uidA gene[27]. Amplification specificity was proven using *P. syringae* gDNA as a non-specific control and a control lacking DNA template (NoT). For this application only, a RPA product was always observed in the NoT control even after numerous precautionary measures were taken to avoid contamination. Moreover, a similar level of amplification was observed in the unrelated DNA template. Hence, we concluded that the RPA kit had low levels of contaminating *E. coli* DNA and the level of amplification in the NoT control could be considered as base line. However, since even *E. coli* negative samples generated amplicons, a false positive may result in the flocculation assay. To overcome this drawback, we "tuned" the assay by increasing the pH of the flocculation buffer from 4.5 to 5. Under this condition, we could account for the background amplification and successfully detect *E. coli* positive samples without false detection in the control samples (FIG. 6B).

Finally, SDG was extended to pathogens causing human diseases such as HIV, malaria, tuberculosis and influenza. To this end, using the same SDG protocol, we successfully distinguished HIV infected cells (proviral DNA) from healthy cells (FIG. 6C). Presence of malarial parasite DNA was also successfully detected in infected blood samples but not in uninfected controls (FIG. 4D). The presence of tuberculosis mycobacteria in culture samples was clearly detectable using two different target genes and could be distinguished from *E. coli* (FIG. 6G). Finally, the influenza A H1N1 virus was detected in infected culture media while uninfected media did not provide any positive signal (FIG. 6H). Taken together, SDG has demonstrated itself as a universal comprehensive approach that can be used in the field, without the need for laboratory processing of samples or sophisticated equipment and can adapted to many applications.

Discussion

Field-ready POC genomic assays may be characterized by a sampling protocol for consistent extraction of fixed amounts of nucleic acids, a rapid and sensitive isothermal amplification method and an equipment-free readout. Herein, we describe the Single Drop Genomics (FIG. 1) assay that integrates all the above characteristics for a universal, virtually equipment-free, low cost method for detecting DNA and RNA from multiple pathogenic and non-pathogenic species across various kingdoms.

Figure 2:
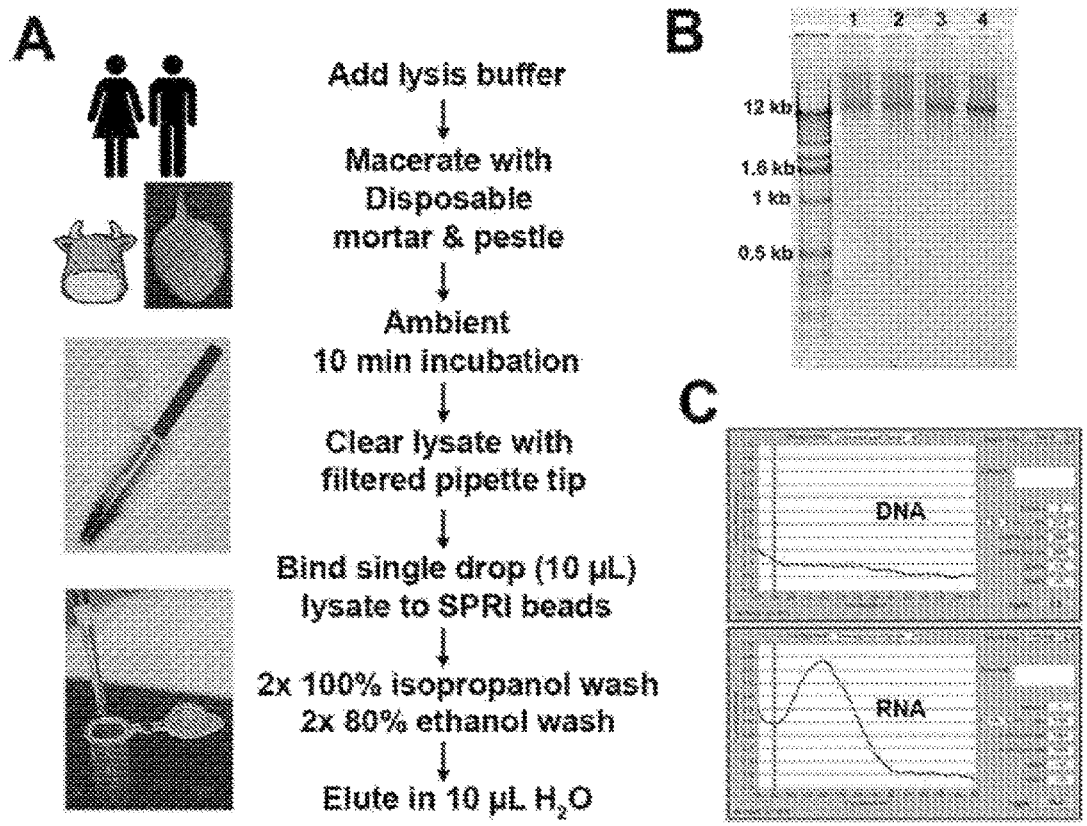
FIG. 2. Precision nucleic acid extraction protocol. (A) Graphical representation of the extraction protocol. Pictures show the possible samples used for extraction, manual maceration of the sample using a disposable mortar and pestle and clearing the lysate of cellular debris using a common filter pipette tip. (B) Gel electrophoresis of four independently extracted DNA samples. The high molecular weight suggests the good integrity of the extracted DNA. (C) Spectrometry analysis of extracted nucleic acids. Top: DNA, Bottom: RNA.

Providing a solution for consistent sampling of nucleic acids to a fixed amount is a non-trivial affair because the amount of input material can significantly affect the performance downstream processes. To achieve this, we have modified established protocols using lysis buffers consisting of chaotropic salts such as guanidium-HCl. Guanidium salts denature proteins and inactivate nucleases thus preserving the integrity of nucleic acids. Together with a detergent, e.g. Triton-X, cellular membranes are broken down to enhance lysis. This is then followed by removal of insoluble cellular debris and finally the extraction and purification of nucleic acids. In laboratory settings, cellular debris is conveniently removed using centrifugation. Unfortunately, centrifuges are not readily available on-field. The cheapest and simplest solution is filtering the crude lysate. As we also sought to achieve this with minimal equipment, we decided to use a common filtered pipette tip as a means to clear the crude lysate (FIG. 2).

Nucleic acids are then extracted using SPRI technology[19] which is the most suitable for POC applications because it is virtually equipment-free; requiring only a magnet. Moreover, DNA yield can be precisely controlled by simply adjusting the amount of SPRI particles given a fixed sample input. Another advantage of this approach is it's relatively low cost. For the amount of SPRI beads used, our approach only cost a few cents and contributed insignificantly to the overall assay cost. With unique combinations of our lysis buffer and SPRI technology, we consistently achieved yields of 3-5 ng/µL for DNA and 30-40 ng/µL for RNA from plant leaf tissue (FIGS. 2B and C). This level of precision is important because in field situations, there are no simple equipment-free ways to quantify nucleic acids. For practical purposes, this concentration of DNA was also optimal for the downstream RPA amplification and did not interfere with the readout assay.

RPA is a relatively new isothermal nucleic acid amplification method[4]. It is commercially available from TWISTDX, has potentially single cell level of detection and up to 5-plex RPA reaction. Another major factor for selecting RPA over other isothermal approaches is that the kits are sold as freeze-dried pellets and are stable at room temperature, a very useful characteristic for applications in geographically remote areas. The RPA assays that we have developed have been designed for sensitive and rapid (30-40 mins) detection of pathogenic or non-pathogenic DNA in plant, animal and human samples.

Figure 3:
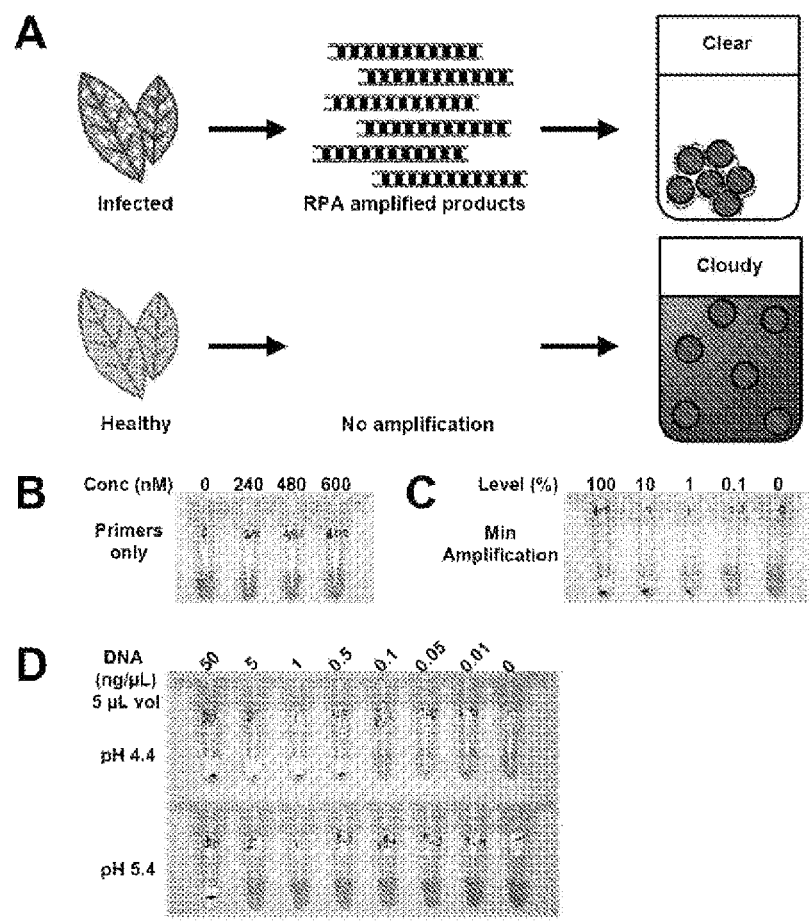
FIG. 3. The flocculation assay. (A) Conceptual representation of the DNA-mediated flocculation of SPRI particles. (B) Excess primers do not mediate flocculation. (C) Only 10% or higher amplification results in flocculation. (D) Cut-off concentration of amplified DNA is dependent on pH.

TWISTDX, the sole commercial supplier of RPA kits, currently markets a portable device which functions as both a heating block and a fluorometer. While this may provide a possible POC solution, the initial outlay to purchase the device and primers with special chemical modifications may pose a limitation for practical implementation. In addition, any kind of equipment used in real field situations will get exposed to adverse climatic conditions that will severely limit the useful life of the instrument, including extreme heat and cold, humidity, dirt, rain, etc. To address this, we developed a readout method that can quickly evaluate RPA amplifications at almost no cost and with no equipment. Our readout approach is a flocculation assay that exploits the high DNA binding abilities of SPRI beads (FIG. 3). To our knowledge, this is the first time the use of magnetic SPRI particles have been described as a readout method. Flocculation assays are advantageous for POC applications primarily because it is simple and does not require sophisticated instrumentation and are useful in applications where simple discrete (yes/no) results are required from a test. Recently various demonstrations using gold nanoparticles for colorimetric biosensing have been described[21-23]. While shown to be very sensitive, the colour shift is relatively subtle unless used in high concentrations and many groups use spectrometry to verify aggregation. In contrast, our flocculation assay has better visual contrast. This is likely due to the larger size of the particles (1 µm) compared to nano-sized gold particles. As the particles floc with increasing DNA loading, they form larger bodies that quickly settle in the tube bottom thus resulting in a clear solution. Free particles, on the other hand, settle slowly resulting in a cloudy solution.

Particle agglutination was also reversible by increasing the buffer pH (FIG. 3D) hence further supporting a DNA-mediated flocculation since, by definition, flocculation is a reversible non-covalent aggregation of colloids.[24] At higher pH, DNA is more negatively charged, hence is more likely to repel other DNA and from the carboxylic acid coated surface of the particles. This pH dependence can also be exploited to tune the assay sensitivity to DNA concentration. In this report, we made use of this characteristic to discriminate between exogenous *E. coli* DNA and contaminant *E. coli* DNA present in the RPA enzyme solution, probably due to the fact that the commercially available enzyme is produced using recombinant techniques from *E. coli* cultures (FIG. 6B). By adjusting the pH to control the flocculation, we could account for the background levels of amplification and hence detect the additional amplification arising from exogenous *E. coli* DNA. While this may be a simple solution, the drawback of this approach is a loss in sensitivity and visual contrast. As the likelihood of flocculation is dependent on the amount of high molecular weight DNA present, it is possible that over-loading the assay with excessive input DNA can also lead to spurious aggregation or false positives. However, due to the precision of our extraction protocol we have effectively avoided this situation (FIG. 2).

Figure 6:
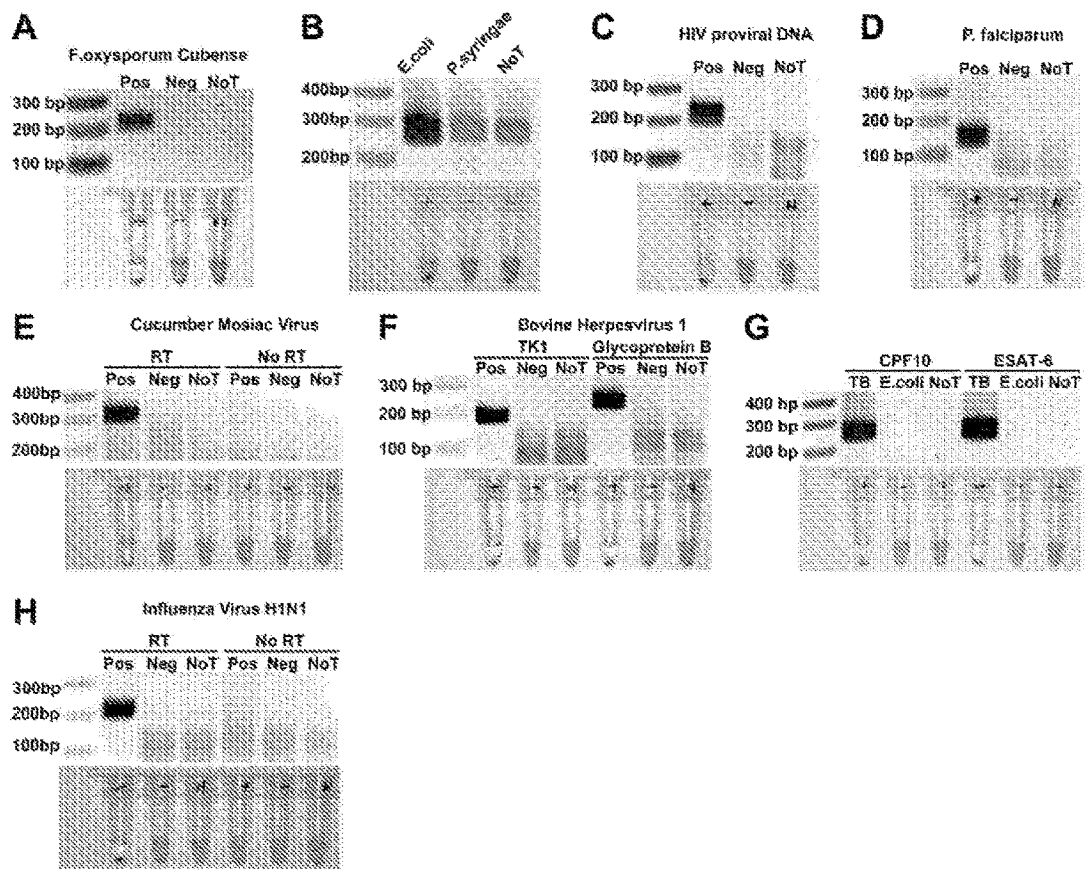
FIG. 6. Single Drop Genomics for detecting multiple pathogens from across various host kingdoms. (A) *F. oxysporum cubense* in banana stems. (B) *Esheriachia. coli* in water using *P. syringae* as an unrelated negative control. (C) HIV proviral DNA in cultured cells. (D) *Plasmodium Falciparum* in blood cultures. (E) Cucumber mosaic virus in tomato leaves. RT: reverse transcriptase. (F) Bovine Herpesvirus 1 in bovine cells using primers targeting the tyrosine kinase 1, TK1 gene and the Glycoprotein B gene. (G) Tuberculosis mycobacteria in cultures using primers targeting the CFP10 and ESAT-6 genes. *E. coli* was used as a negative control. (H) Influenza virus H1N1 in culture media. Top row: gel electrophoresis images of RPA reactions. Bottom row: photographs of the flocculation assay corresponding to the RPA reactions. Pos: positive (infected) sample. Neg: negative (uninfected) sample. NoT: no template control. RT: reverse transcriptase.

Finally, the broad gamut of applications of SDG was demonstrated through the successful detection of a plethora of pathogens directly from various host specimens (FIG. 6). For example we detected fungi, bacteria, and virus in plants; herpes viral DNA in bovine cells; HIV proviral DNA, malaria parasites in human tissue, influenza A H1N1 viruses and bacteria-laced water. The multispecies examples shown here demonstrate the wide potential and versatility for other on-field testing applications in remote locations.

In conclusion, the Single Drop Genomic assay is a comprehensive, field-ready, universal, equipment-free, multispecies DNA and RNA detection strategy with a plethora of applications in agriculture, human health and general biosafety. SDG in its current form is ready for on-field evaluation.

TABLE 1

| Target | 5'-Forward-3' | 5'-Reverse-3' |
| --- | --- | --- |
| F. oxysporum f.sp. conglutinans | GCTCTTGATTTAGGTAC AACTCTTTCCCTCGTC (SEQ ID NO: 1) | ATATATCTGTATAGGAA TCCCACTGAATTTTTC (SEQ ID NO: 2) |
| Botrytis cinerea | TTTCCACAGGGTTTGTG TACGAGATTGGTATTC (SEQ ID NO: 3) | TTCTCCGGTGTCCGTTC GCACTGTAGACAATCG (SEQ ID NO: 4) |
| Pseudomonas syringae | TTTGTCCGAAACGACGT ACAGCCATTTAACCTT (SEQ ID NO: 5) | TTCTACGTCGGGGTATT TACTAGCTGGAAAAG (SEQ ID NO: 6) |
| F. oxysporum cubense | ATTGAAGGACTCATACA AGGTTGCATCAAAATA (SEQ ID NO: 7) | TTTCCTTTTGCAACTCC TACAGAGTGTCTATAA (SEQ ID NO: 8) |
| Cucumber mosaic virus RNA3 Coat | AGTTAATCCTTTGCCGA AATTTGATTCTAC (SEQ ID NO: 9) | GTGCTCGATGTCAACAT GAAGTACTAGCTC (SEQ ID NO: 10) |
| Bovine HPV TK1 | GGAAGATCTGCTCATGC TCGCGGCCGCCATGCC (SEQ ID NO: 11) | GAGCGCGTAAGCATTGC GCACAGCGACCAGAAA (SEQ ID NO: 12) |
| Bovine HPV Glycoprotein B | AAGTGGCGCGAGGCGGA CGAAATGCTGCGAGAC (SEQ ID NO: 13) | ACGTGCGTGCCGTTGTA GCGCTCGCGGTAGACG (SEQ ID NO: 14) |
| E. coli uidA gene | CTGTGACGCACAGTTCA TAGAGATAACCTTC (SEQ ID NO: 15) | AAAAGCAGTCTTACTTC CATGATTTCTTTAACT (SEQ ID NO: 16) |
| HIV | AAATTAACAATTACACA AGCTTAATACACTCC (SEQ ID NO: 17) | TATAGAAAGTACAGCAA AAACTATTCTTAAACC (SEQ ID NO: 18) |
| Plasmodium Falsiparum MSP1 | TTGAAGGAAGTAAGAAA ACAATTGATCAAAATA (SEQ ID NO. 19) | CTAAAACGCTTATTAAA TTATGTGCTTCTTCTA (SEQ ID NO: 20) |
| Tuberculosis CFP10 | ATTTTGGCGAGGAAGGT AAAGAGAGAAAGTAGT (SEQ ID NO: 21) | GAGTTCCTGCTTCTGCT TATTGGCTGCTTCTT (SEQ ID NO: 22) |
| Tuberculosis ESAT-6 | CAATCCAGGGAAATGTC ACGTCCATTCATTCC (SEQ ID NO: 23) | CCTATGCGAACATCCCA GTGACGTTGCCTTC (SEQ ID NO: 24) |

Example 2

Rapid, Low-Resource Evaluation of Locus-Specific DNA Methylation with DNA-Mediated Bridging Flocculation The challenge of bringing DNA methylation biomarkers into clinic is the lack of simple methodologies as most assays have been developed for research purposes. Herein we describe a highly modified methyl-protein domain (MBD) enrichment protocol coupled with a DNA-mediated flocculation assay for rapid yet highly stringent, naked-eye binary evaluation of highly methylated locus-specific regions from nanogram amounts of input. The low resource requirements of our method may enable widespread adoption of DNA methylation-base diagnostics in clinic and may be useful for small-scale research.

Material and Methods
DNA Sample Preparation

Whole genome amplified (WGA) DNA was generated using the REPLI-g UltraFast Mini kit (Qiagen) and purified using the DNeasy Blood and Tissue kit (Qiagen). An aliquot of WGA DNA was then treated with SssI methyltransferase overnight and purified to generate highly methylated genomic DNA. Cell line derived DNA was also purified with the DNeasy Blood and Tissue kit. Cell lines were purchased from ATCC and cultured according to the manufacturer's recommendation.

Whole blood DNA from prostate cancer patients were purified using a modified SPRI protocol[28]. Briefly, 60 µL of whole blood preserved with EDTA was incubated with 10 µL of proteinase K solution (New England Biolabs, NEB), 60 µL of lysis buffer (3 M Guanidine HCl, 2% Triton X) and 2 µL of RNase A solution (4 mg/mL) for 10 minutes at room temperature. 10 µL of carboxyl coated magnetic beads (Thermo Fisher) and 240 µL binding buffer (100 mM Tris-HCl, 2.5 M NaCl, 20% w/v PEG8000, pH 8.0) was then added to the lysed blood. After a 10 min incubation at room temperature, DNA bound magnetic beads were collected with a magnet and washed once with a wash solution (400 mM Guanidine HCl, 70% ethanol), twice with 70% ethanol and finally eluted in 30 µL of water. Both blood samples were processed within 24 hours of collection. Approval to use human blood sample was granted by the local ethics committee.

To generate DNA fragment sizes compatible with MDB enrichment, MseI and MluCI restriction enzymes (NEB) were used. Briefly, 50 ng of DNA was digested with 1 unit of each enzyme in a 10 µL reaction at 37° C. for 30 mins After digestion, 2 µL of the reaction was used for each MBD enrichment.

MBD Enrichment

The Epimark Methylated DNA Enrichment kit (NEB) was used with major modifications to the recommended instructions. Briefly, 2 µg MDB2a-Fc protein was incubated with 10 µL of Protein A magnetic beads at room temperature for 15 minutes. 0.5 µL of the MBD/magnetic bead mix was then used for each 50 µL enrichment reaction in a 1×MBD buffer with NaCl modified to a concentration of 300 mM. DNA was reacted with the MBD/magnetic beads for 15 mins on ice. This was then followed by three 5 minute washes with 1×MBD buffer with NaCl modified to 300 mM to remove excess and weakly bound DNA. Enriched DNA was then eluted with 5 µL of 2.5 M NaCl solution. Finally, enriched DNA was purified with Agencourt AMPure XP SPRI magnetic beads (Beckman Coulter) according the manufacture recommendations and eluted in 6 µL of water. 1 µL purified DNA was then used for each RPA reaction.

RPA Amplification

RPA reactions were performed using the TwistAmp Basic Kit (TWISTDX) with some modifications to the recommended protocol. Briefly, 500 nM primers were used in each 12.5 µL reaction supplemented with 7 mM MgOAc. After a rapid 20 min RPA amplification, 3 µL was electrophoresed on a gel to verify amplification. The remaining was subjected a SPRI clean-up was performed to remove RPA reaction components that could interfere with the downstream flocculation assay. Purified amplicons were then eluted in 9.5 µL water.

Flocculation Assay

To perform the flocculation assay, 3 µL of purified RPA amplicons were incubated with 6 µL of Agencourt AMPure XP SPRI magnetic beads at room temperature for 5 minutes. Beads were then captured with a magnet and the supernatant was removed. 20 µL flocculation buffer (200 mM Acetate Buffer pH 4.4) was then added immediately and allowed to incubate for an additional minute on the magnet. Finally, tubes were then removed from the magnet and agitated by gently tapping the sides of the tubes. Positive test result in a flocculate of DNA/bead pellet while beads readily redispersed into solution negative tests.

Epigenetic changes in DNA are potential disease biomarkers.[28] One form of DNA epigenetic change is the methylation of the cytosine (5mC) in cytosine/guanine dinucleotide (CpG), particularly in CpG islands (CGI) of promoter regions that function to regulate cellular processes. Most approaches however, detect DNA methylation via bisulfite conversion[29,30] of DNA followed by some form of sequencing.[31-34] To avoid the complications associated with bisulfite conversion approaches, affinity capture methods using Methyl-Binding Domain (MDB) proteins or antibodies raised against 5-methylcytosine have been adopted, usually coupled to next generation sequencing (NGS), in many recent DNA methylation studies.[35,36] While these methods are excellent for research, simpler and more convenient methods to detect gene-specific methylation for routine diagnostics are still lacking. Although various strategies have been developed with affinity-based approaches[34-40] to address clinical needs while avoiding the bisulfite treatment, all approaches still require some form of an optical readout method to evaluate differentially methylated regions (DMRs).

A useful characteristic of MBD-enrichment methods is the almost binary specificity of the enzymes under the appropriate salt concentrations[35,36], i.e., either MDB captures methylated DNA or not. This binary characteristic may be useful in situations where significant changes e.g., regions of high differential methylation (HDMRs) that are predictive of disease outcomes in clinic. Therefore, a readout method mirroring these digital yes/no biomarkers may be useful. A possible binary readout approach could be a DNA polymer-mediated bridging flocculation assay. As flocculation typically occurs abruptly between phases[41-47], marrying MDB enrichment assays with a flocculation-based readout may result in a rapid, low-resource method to evaluate HDMRs.

The key feature of the bridging flocculation process is to discriminate between long and short DNA polymer segments which lies at the heart of enabling the assay. Since bridging flocculation is easily seen with the naked eye, it is a very attractive low resource evaluation system compared to conventional methodologies and may be more suited for low cost routine clinical use. In contrast to other nanoparticle-based approaches[21-24] where the colour shifts are usually subtle and require spectrometry for verification, the shift from cloudy to a clear solution in a flocculation assay has better visual contrast and can easily be evaluated by naked eye without additional equipment.

Results & Discussion

Figure 7:
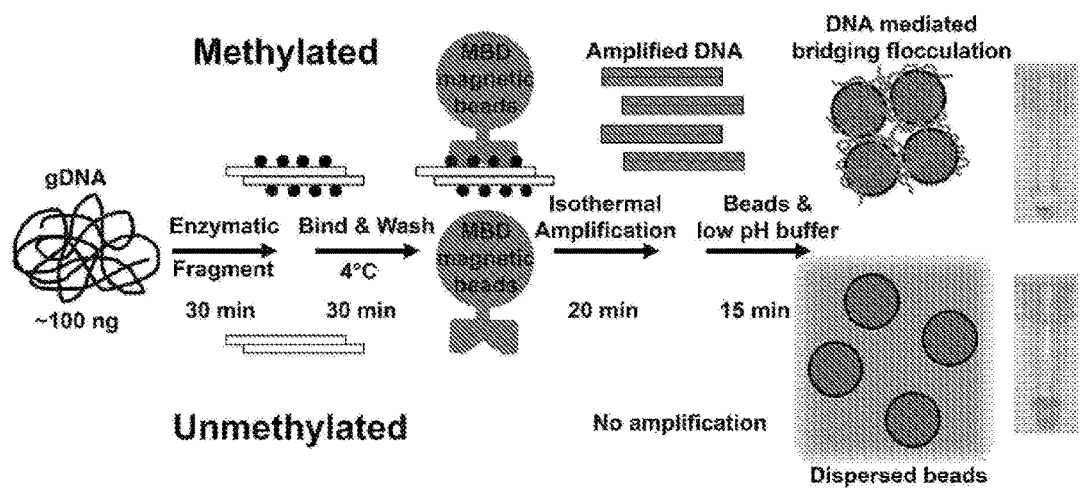
FIG. 7. Schematic of the assay. 1) Genomic DNA is enzymatically fragmented to sizes compatible with Methyl binding domain (MBD) enrichment. 2) Rapid high stringency enrichment of methylated DNA is performed on ice (4° C.). 3) Regions of interests are amplified via an isothermal method. 4) The presence of long amplified DNA induces a bridging flocculation which indicates the presence of the high differentially methylated region (HDMR) of interest.

Herein, we describe a novel method (FIG. 7) using MBDs to selectively enrich for methylated DNA, followed by the robust isothermal recombinase polymerase amplification (RPA)[4] to generate large amounts of HDMR-specific DNA polymers. Finally, the presence of the amplified HDMR is evaluated by naked eye via a DNA-mediated bridging flocculation assay. Only nanogram amounts of starting genomic material was required and the assay was sensitive to 10% changes in methylation under current conditions. The assay was completed in under two hours and required only minimal equipment: pipettes, a heating block and a magnet. Finally, the assay was applied to a panel of cells and whole blood-derived DNA to test for the presence of three potential cancer-related HDMRs. We believe the speed, simplicity and low resource requirement of the method could have broad DNA methylation-based applications in the clinic.

Figure 8:
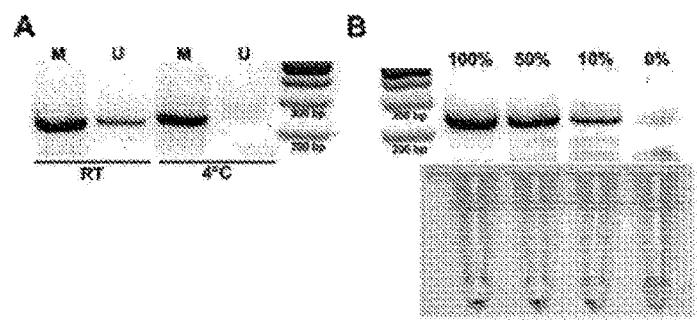
FIG. 8. (A) Gel electrophoresis image of RPA products using ESR1 primers demonstrating improved stringency of MDB enrichment at low temperatures (4° C.) without a lost in performance as compared to the assay performed at room temperature (RT). M: methylated control, U: unmethylated control. (B) Top: Gel electrophoresis image of RPA reactions using ESR1 primers for DNA inputs at various levels of methylation. Bottom: Photos showing flocculation occurring from as little as 10% methylated samples.

To realise the method (FIG. 7), we first enzymatically fragmented 50 ng of genomic DNA (gDNA) for the MBD enrichment. We chose enzymatic fragmentation of input DNA because it was an established and robust molecular technique that required only a heating block unlike physical shearing by sonication which may be time consuming and requires specialized equipment. The combination of the MseI and MluCI restriction enzymes (recognition sequence: TTAA and AATT respectively) were selected because they cut frequently in the human genome to generate fragments (125 bp on average) compatible with MBD enrichment while avoiding excessive fragmentation of CGIs where HDMRs are typically found. Next, MBD coupled to magnetic beads were then introduced to select for HDMRs in a relatively high salt (300 mM) buffer[36] while performing both the binding and washing steps on ice (4° C.) to enable rapid yet high stringency enrichment. Using primers against the CGI associated with the ESR1 gene promoter, a known HDMR in breast cancer[27], we first tested the MBD enrichment step with 5 ng of whole genome amplified (WGA) DNA as an unmethylated control against 5 ng WGA DNA methylated in vitro as the methylated control. As indicated by subsequent RPA amplification of enriched DNA, performing the whole MBD assay (binding and washing) on ice resulted in highly specific enrichment of only methylated DNA with minimal loss in performance in about 30 minutes (FIG. 8A). This a significant improvement in both speed and specificity over protocols previously described[36,38] where either cocktails of different MDB enzymes and/or overnight incubations at 4° C. were needed to achieve high stringency with low input. Moreover, the robust and rapid isothermal amplification used here further simplified and hastened the assay.

As naked-eye evaluations may be useful for binary diagnostic outcomes such as MBD enriched HDMRs, we used a flocculation assay to evaluate amplification. As only minimal equipment is needed for evaluation, a flocculation assay may also be suitable for low resource settings. Following RPA amplification for HDMRs of interest we used, as a proof-of-concept, the solid phase reversible immobilization (SPRI)[28] carboxylic-coated magnetic beads for DNA purification to precipitate DNA onto the surface of the beads. Then instead of eluting the bound DNA, a low pH buffer was introduce to trigger a flocculate only if high amounts of RPA amplicons with sufficient lengths were present, which in turn represents the presence of the MBD-enriched HDMR. If no amplification occur, indicating a lack of methylation, the 1 µm beads readily disperse into solution. To our knowledge, this is a first bridging flocculation assay for a MBD/RPA-based approach.

Confident that we could now rapidly detected HDMRs with high stringency, we turned our attention to determining the detection limits of the assay, specifically (1) the minimum input needed to generate enough RPA amplicons to trigger a flocculate and (2) the minimum detectable amount of methylated DNA. To this end, we processed 5 ng of gDNA titrated to various level of methylation (100%, 50%, 10% and 0%). We could robustly detect the presence of methylated DNA from as little as 10% of the total DNA input was methylated on both gel electrophoresis visualization and with the flocculation assay (FIG. 2B). This also suggested that a minimum of 0.5 ng (10% methylated sample) of starting methylated DNA was required for a detectable signal. Considering these data, we were confident that our approach was both specific and sensitive to highly methylated DNA in the nanogram regime.

Recently an on-chip MBD/RPA approach using DNA-induced shifts in magnetic resonance[10] was described. While rapid and useful, the approach requires auxiliary equipment to evaluate the presence of RPA amplicons. In contrast, results are easily evaluated with the naked eye by our approach within a similar timeframe and with less starting material. In addition, we have also demonstrated the ability of our method to detect low level (10%) methylation, albeit qualitatively, and from nanogram amounts of DNA input.

Figure 9:
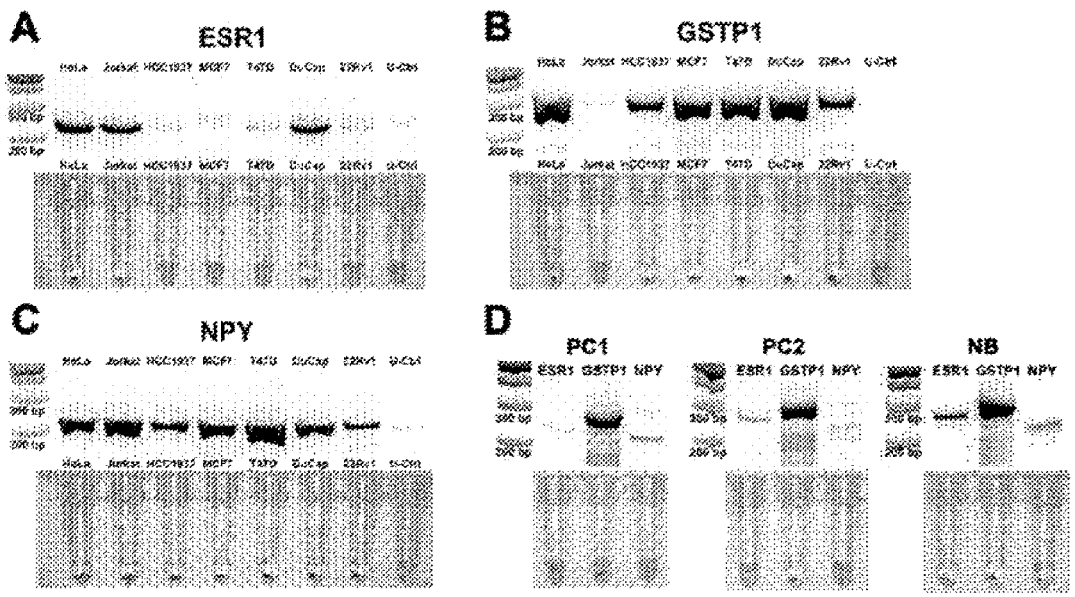
FIG. 9. Methylation profiles of 7 human cancer cell lines for (A) ESR1, (B) GSTP1 and (C) NPY. Unmethylated controls (U-Ctrl) was included to validate assay stringency.

Finally, to demonstrate an application on more complex biological samples, we extended our assay to evaluate the methylation status of two additional potential biomarkers GSTP1[49-51] and NPY[52-54] in addition to ESR1 on a panel of human cancer cell lines (FIG. 9A-C). To control for stringency, unmethylated WGA DNA was also assayed simultaneously with the cell line-derived DNA. As expected, for all three biomarker assays, negligible RPA amplification were detected in the unmethylated controls thus validating assay stringency. As expected, we successfully profiled the methylation states of ESR1, NPY and GSTP1 for all 7 cell line samples. In addition, the data presented here were consistent with the literature[55,56], thus underscoring the accuracy of our approach. Finally, we applied the assay to two samples of whole blood derived gDNA obtained from men with highly metastatic prostate cancer and one from a pooled sample of 25 normal females (FIG. 3D). For the two prostate cancer samples (PC1 and PC2), highly methylated GSTP1 was detected but not for ESR1 and NPY based on the presence of a flocculate. For the pooled normal DNA sample (NB), all three biomarkers were methylated as indicated by the flocculation assay. While the methylation profiles were unexpected for the normal DNA sample, further investigation is outside the scope of this report. However the data underscores the importance of selecting the appropriate sampling source for specific methylation biomarkers. Nonetheless, the results here demonstrate the feasibility of our assay with bodily fluids (e.g. whole blood) typically used in routine diagnostics.

In conclusion, we describe for the first time a rapid MBD-based method for stringent enrichment of methylated DNA from nanogram amounts of input. Coupling this with RPA, we could achieve sensitive detection from at least 10% methylated samples. Positive MBD/RPA results are then evaluated by naked eye with a simple flocculation assay and is also the first demonstration of a classical colloid chemistry phenomena for methylation detection. The method was also extended to cell line and whole blood derived samples to demonstrate its feasibility as a diagnostic tool. Finally, the use of a flocculation assay to evaluate positive MBD/RPA results enables a label-free approach for low resource applications that may be beneficial for routine diagnostics and small-scaled DNA methylation research.

Example 3

Urinary TMPRSS2:ERG Fusion Detection in Prostate Cancer

TMPRSS2-ERG gene fusions are the predominant molecular subtype of prostate cancer. Considerable evidence suggests that TMPRSS2-ERG fusions mediate tumour invasion, consistent with the defining histologic distinction between prostatic intraepithelial neoplasia (PIN), a precursor lesion of prostate cancer and prostate cancer itself. It is therefore of value to determine whether the "single drop" nucleic acid detection system disclosed herein can detect TMPRSS2-ERG gene fusions in a manner that could be useful for point-of-care diagnostics.

Isothermal recombinase polymerase amplification was performed under conditions essentially as previously described using the primers set forth in Table 2. Amplicons were then detected using SPRI particles in a flocculation inducing buffer under conditions essentially as previously described.

As shown in FIG. 10, DNA sequencing of DuCap RNA amplicons after RT-RPA. RT-RPA amplicons of extracted DuCap RNA was purified using SPRI magnetic beads and sequenced, which verified amplification of the target TMPRSS2:ERG region. FIG. 11 shows RT-PCR of extracted RNA from urine specimens of 10 metastatic castrate-resistant prostate cancer patients and a healthy patient. The RT-PCR amplicons visualized by agarose gel electrophoresis validated the screening results of the flocculation assay on the same group of patients (FIG. 11c). In FIG. 12 a comparison of RNA stability in whole urine and urinary sediments demonstrates RT-RPA of patient whole urine and urinary sediment RNA extracted at 0, 2 and 12 hrs after specimen collection.

In summary, these data show that the "single drop genomics" concept disclosed herein is ideally suited to the rapid and efficient detection of nucleic acids comprising TMPRSS2-ERG gene fusions as a diagnostic indicator of the potential presence of prostate cancer cells.

TABLE 2

| Oligonucleotides | Sequence (5' to 3') |
|---|---|
| RT-RPA Forward, RT-PCA Forward | CCTGGAGCGCGGCAGGAAGCCTTATCAGTTG (SEQ ID NO: 25) |
| RT-RPA Reverse | GCTAGGGTTACATTCCATTTTGATGGTGAC (SEQ ID NO: 26) |
| RT-PCR Reverse | TCCTGCTGAGGGACGCGTGGGCTCATCTTG (SEQ ID NO: 27) |

Oligonucleotides were purchased from Integrated DNA Technologies

Example 4

Rolling Circle Amplification Generation of Amplicons for Single Drop Genomics

Rolling Circle Amplification (RCA) is a rapid isothermal nucleic acid amplification that method has been used extensively for the detection disease biomarkers.[57-59] As RCA generates long (kilobases) of DNA polymers, it may be amenable to a DNA mediated bridging flocculation readout which requires sufficient DNA of appropriate lengths. The advantage of a DNA mediated bridging flocculation readout assay is that results can be evaluated on site with the naked eye and therefore useful for applications in low resource settings. In this study, we demonstrated the feasibility of combining RCA amplification with a bridging flocculation readout for rapid, low resource detection of the agriculturally important pathogen *Pseudomonas syringae* (PSY).

Materials & Methods

Circle Probe Design

The *Pseudomonas syringae* (Psy) genome sequence was obtained from GenBank, National Center for Biotechnology Information (NCBI). Bioinformatic analysis was performed and candidate target Psy sequences were identified. Candidate sequences were subjected to BLAST searches to identify homologous DNA fragments in other organisms. Special attention was devoted to find sequences present in the Psy genome but absent from other organism. A fragment showing no homology to any available sequence in the databank was chosen. Based on the unique sequence, CViPII nicking sites were identified and a single stranded circle probe was designed with 64 nt sequence 5'-TGGTCT-TAAAAACTCTTTCGTTGTCATTGGGATAGGCGAT-TCTAA ATTTCTCAACGAAATCTGG-3' ("Nick PSY"; SEQ ID NO:28).

Circular probe was prepared by mixing the 10 pmol of single stranded circle probe with 5U of CircLigase II (Epicentre) in 20 μl reaction containing 1× CircLigase II reaction buffer (33 mM Tris-acetate (pH 7.5), 66 mM potassium acetate, and 0.5 mM DTT), 2.5 mM $MnCl_2$ and 1M betaine. The reaction was incubated at 60° C. for 16 hr and followed by 80° C. for 10 min to inactivate the CircLigase II.

Digestion of Genomic DNA 50 ng of Psy genomic DNA and plant genomic DNA were digested with 5U of CViPII nicking enzyme (NEB) in 20 μl reaction containing 1× CutSmart buffer (50 mM Potassium Acetate, 20 mM Tris-acetate, 10 mM Magnesium Acetate, 100 μg/ml BSA). The digestion was initially incubated at 37° C. for 90 min followed by denaturation step at 65° C. for 20 min.

Rolling Circle Amplification (RCA)

100 nM of circle probe was mixed with 250 pg of nicking enzyme digested genomic DNA in 20 μl reaction containing 5U of Klenow fragment (3'→5' exo) (NEB), 5U of Phi29 DNA polymerase (NEB) and 125 nM of each dNTP in 1× Phi29 buffer (50 mM Tris-HCl, 10 mM $MgCl_2$, 10 mM $(NH_4)_2SO_4$, 4 mM DTT). The reaction mixture was incubated at 37° C. for 30 min. The products were analyzed by gel electrophoresis using 1.5% agarose gels in sodium borate buffer. Due to the nature of a linear RCA, the expected product sizes ranged from as short as 25 bases to an excess of 10 as indicated via gel electrophoresis.

Flocculation Assay

5 μL of RCA reaction was incubated with 10 μL of Agencourt Ampure XP SPRI beads for 5 minutes at room temperature to bind RCA products onto the magnetic bead surface. DNA loaded beads were then isolated with a magnet and washed once with 70% ethanol and allowed to air dry for 1 minute. 30 μL of flocculation buffer (100 mM acetate buffer, pH 4.4) was then added to beads and incubated for another 1 minute before agitation by gently tapping the sides of the tube.

Results & Discussion

To realise the application, we first spiked PSY genomic DNA (gDNA) into a 5 ng background of host plant gDNA (Arabidopsis thaliana, FIG. 13). As expected, high molecular weight products, indicated by a laddering/smearing profile, were generated only in the presence of PSY (1-10%) but not in plant DNA (0%) indicating the specificity of the RCA assay. Additionally, a DNA mediated flocculate appeared only when RCA was successful (1-10% spike samples) thus demonstrating the feasibility of the flocculation readout for RCA generated products.

Finally, to simulate an actual agriculture application, we harvested host plant leaves representing the phenotype at various degrees of infection (S1-5, FIG. 14). Using RCA and the flocculation readout, we could detect the presence of PSY as early as S1 which represents the pre-symptomatic levels of infection. No amplification and therefore no flocculate was seen with healthy (H) and no template (NoT) controls, indicating the specificity of the approach.

In conclusion, the DNA mediated bridging flocculation readout was compatible with RCA generated products and may be useful for rapid, sensitive, low resource detection of pathogen sequences. The application of the flocculation assay for RCA generated products was demonstrated with the successful detection of PSY in infected host plant leaves.

Throughout the specification, the aim has been to describe the preferred embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety.

REFERENCES

1 Barany, F. The ligase chain reaction in a PCR world. *PCR Methods Appl* 1, 5-16 (1991).
2 Craw, P. & Balachandran, W. Isothermal nucleic acid amplification technologies for point-of-care diagnostics: a critical review. *Lab Chip* 12, 2469-2486 (2012).
3 Gill, P. & Ghaemi, A. Nucleic acid isothermal amplification technologies—A review. *Nucleos Nucleot Nucl* 27, 224-243 (2008).
4 Piepenburg, O., Williams, C. H., Stemple, D. L. & Armes, N. A. DNA detection using recombination proteins. *Plos Biol* 4, 1115-1121 (2006).
5 Vincent, M., Xu, Y. & Kong, H. M. Helicase-dependent isothermal DNA amplification. *Embo Rep* 5, 795-800, doi:DOI 10.1038/sj.embor.7400200 (2004).
6 Rohrman, B. A. & Richards-Kortum, R. R. A paper and plastic device for performing recombinase polymerase amplification of HIV DNA. *Lab Chip* 12, 3082-3088, doi:Doi 10.1039/C21c40423k (2012).
7 Lutz, S. et al. Microfluidic lab-on-a-foil for nucleic acid analysis based on isothermal recombinase polymerase amplification (RPA). *Lab Chip* 10, 887-893, doi:Doi 10.1039/B921140c (2010).
8 Mahalanabis, M., Do, J., ALMuayad, H., Zhang, J. Y. & Klapperich, C. M. An integrated disposable device for DNA extraction and helicase dependent amplification. *Biomed Microdevices* 12, 353-359 (2010).
9 Chow, W. H. A. et al. Application of isothermal helicase-dependent amplification with a disposable detection device in a simple sensitive stool test for toxigenic *Clostridium difficile*. *J Mol Diagn* 10, 452-458 (2008).
10 Agrios, G. N. Plant pathology. 5th edn, (Elsevier Academic Press, 2005).
11 Horsfall, J. G. & Cowling, E. B. *Plant disease: an advanced treatise*. (Academic Press, 1977).
12 Kokoskova, B. & Janse, J. D. Enzyme-linked immunosorbent assay for the detection and identification of plant pathogenic bacteria (in particular for *Erwinia amylovora* and *Clavibacter michiganensis* subsp. *sepedonicus*). *Methods in molecular biology* 508, 75-87, doi: 10.1007/978-1-59745-062-1_7 (2009).
13 Wang, Z. H. et al. Development of an ID-ELISA for the detection of Rice black-streaked dwarf virus in plants. *Journal of virological methods* 134, 61-65, doi:10.1016/j.jviromet.2005.11.019 (2006).
14 Wright, S. F. & Morton, J. B. Detection of vesicular-arbuscular mycorrhizal fungus colonization of roots by using a dot-immunoblot assay. *Applied and environmental microbiology* 55, 761-763 (1989).

15 Heiny, D. K. G., D. G. Enzyme-linked immunosorbent assay, immunoblot detection, and antibody neutralization of *Stemphylium botryosum* phytotoxin. *Physiological and Molecular Plant Pathology* 35, 439-451, doi:10.1016/0885-5765(89)90063-5 (1989).

16 Janse, J. D. & Kokoskova, B. Indirect immunofluorescence microscopy for the detection and identification of plant pathogenic bacteria (in particular for *Ralstonla solanacearum*). *Methods in molecular biology* 508, 89-99 (2009).

17 Price, J. A., Smith, J., Simmons, A., Fellers, J. & Rush, C. M. Multiplex real-time RT-PCR for detection of Wheat streak mosaic virus and *Triticum* mosaic virus. *Journal of virological methods* 165, 198-201, doi:10.1016/j.jviromet.2010.01.019 (2010).

18 Dai, J., Peng, H., Chen, W., Cheng, J. & Wu, Y. Development of multiplex real-time PCR for simultaneous detection of three Potyviruses in tobacco plants. *Journal of applied microbiology* 114, 502-508, doi: 10.1111/jam.12071 (2013).

19 Deangelis, M. M., Wang, D. G. & Hawkins, T. L. Solid-Phase Reversible Immobilization for the Isolation of Pcr Products. *Nucleic Acids Res* 23, 4742-4743 (1995).

20 Rohland, N. & Reich, D. Cost-effective, high-throughput DNA sequencing libraries for multiplexed target capture. *Genome research* 22, 939-946, doi:10.1101/gr.128124.111 (2012).

21 Xia, F. et al. Colorimetric detection of DNA, small molecules, proteins, and ions using unmodified gold nanoparticles and conjugated polyelectrolytes. *P Natl Acad Sci USA* 107, 10837-10841 (2010).

22 Xu, X. W., Wang, J., Yang, F., Jiao, K. & Yang, X. R. Label-Free Colorimetric Detection of Small Molecules Utilizing DNA Oligonucleotides and Silver Nanoparticles. *Small* 5, 2669-2672 (2009).

23 Li, H. X. & Rothberg, L. Colorimetric detection of DNA sequences based on electrostatic interactions with unmodified gold nanoparticles. *P Natl Acad Sci USA* 101, 14036-14039 (2004).

24 Hunter, R. J. *Foundations of colloid science*. 2nd edn, (Oxford University Press, 2001).

25 Euler, M. et al. Recombinase polymerase amplification assay for rapid detection of Rift Valley fever virus. *J Clin Virol* 54, 308-312, doi:10.1016/j.jcv.2012.05.006 (2012).

26 Euler, M. et al. Development of a panel of recombinase polymerase amplification assays for detection of biothreat agents. *J Clin Microbiol* 51, 1110-1117, doi:10.1128/JCM.02704-12 (2013).

27 Maheux, A. F. et al. Analytical comparison of nine PCR primer sets designed to detect the presence of *Escherichia coli/Shigella* in water samples. *Water Res* 43, 3019-3028 (2009).

28. Klose, R. J. & Bird, A. P. Genomic DNA methylation: the mark and its mediators. *Trends Biochem Sci* 31, 89-97 (2006).

29. Frommer, M. et al. A genomic sequencing protocol that yields a positive display of 5-methylcytosine residues in individual DNA strands. *Proc Natl Acad Sci USA* 89, 1827-1831 (1992).

30. Clark, S. J., Harrison, J., Paul, C. L. & Frommer, M. High sensitivity mapping of methylated cytosines. *Nucleic Acids Res* 22, 2990-2997 (1994).

31. Taylor, K. H. et al. Ultradeep bisulfite sequencing analysis of DNA methylation patterns in multiple gene promoters by 454 sequencing. *Cancer Res* 67, 8511-8518 (2007).

32. Gu, H. et al. Preparation of reduced representation bisulfite sequencing libraries for genome-scale DNA methylation profiling. *Nat Protoc* 6, 468-481 (2011).

33. Hirst, M. & Marra, M. A. Next generation sequencing based approaches to epigenomics. *Brief Funct Genomics* 9, 455-465 (2010).

34. Zerilli, F. et al. Methylation-specific loop-mediated isothermal amplification for detecting hypermethylated DNA in simplex and multiplex formats. *Clinical chemistry* 56, 1287-1296 (2010).

35. Nair, S. S. et al. Comparison of methyl-DNA immunoprecipitation (MeDIP) and methyl-CpG binding domain (MBD) protein capture for genome-wide DNA methylation analysis reveal CpG sequence coverage bias. *Epigenetics: official journal of the DNA Methylation Society* 6, 34-44 (2011).

36. Warton, K. et al. Methylation-capture and Next-Generation Sequencing of free circulating DNA from human plasma. *BMC genomics* 15, 476 (2014).

37. Lee, T. Y., Shin, Y. & Park, M. K. A simple, low-cost, and rapid device for a DNA methylation-specific amplification/detection system using a flexible plastic and silicon complex. *Lab on a chip* (2014).

38. Oliver, V. F. et al. A novel methyl-binding domain protein enrichment method for identifying genome-wide tissue-specific DNA methylation from nanogram DNA samples. *Epigenetics & chromatin* 6, 17 (2013).

39. Corrie, S. R. et al. Bisulfite-free analysis of 5MeC-binding proteins and locus-specific methylation density using a microparticle-based flow cytometry assay. *The Analyst* 136, 688-691 (2011).

40. Wee, E. J. & Trau, M. Measuring whole genome methylation via oxygen channelling chemistry. *Chemical communications* 50, 10894-10896 (2014).

41. Ruehrwein, R. A. & Ward, D. W. Mechanism of Clay Aggregation By Polyelectrolytes. *Soil Science* 73, 485-492 (1952).

42. La Mer, V. K. Filtration of colloidal dispersions flocculated by anionic and cationic polyelectrolytes. *Discussions of the Faraday Society* 42, 248-254 (1966).

43. Healy, T. W. & La Mer, V. K. The energetics of flocculation and redispersion by polymers. *Journal of Colloid Science* 19, 323-332 (1964).

44. Smellie Jr, R. H. & La Mer, V. K. Flocculation, subsidence and filtration of phosphate slimes: VI. A quantitative theory of filtration of flocculated suspensions. *Journal of Colloid Science* 13, 589-599 (1958).

45. Flory, P. J. Thermodynamics of high polymer solutions. *J Chem Phys* 9, 660-661 (1941).

46. Flory, P. I. Thermodynamics of high polymer solutions. *J Chem Phys* 10, 51-61 (1942).

47. Huggins, M. L. Solutions of long chain compounds. *J Chem Phys* 9, 440-440 (1941).

48. Widschwendter, M. et al. Association of breast cancer DNA methylation profiles with hormone receptor status and response to tamoxifen. *Cancer research* 64, 3807-3813 (2004).

49. Rand, K. N. et al. Headloop suppression PCR and its application to selective amplification of methylated DNA sequences. *Nucleic Acids Res* 33, e127 (2005).

50. Lee, W. H. et al. Cytidine methylation of regulatory sequences near the pi-class glutathione S-transferase gene accompanies human prostatic carcinogenesis. *Proc Natl Acad Sci USA* 91, 11733-11737 (1994).

51. Millar, D. S. et al. Detailed methylation analysis of the glutathione S-transferase pi (GSTP1) gene in prostate cancer. *Oncogene* 18, 1313-1324 (1999).

52. Roperch, J. P. et al. Aberrant methylation of NPY, PENK, and WIF1 as a promising marker for blood-based diagnosis of colorectal cancer. *BMC cancer* 13, 566 (2013).
53. Bediaga, N. G. et al. DNA methylation epigenotypes in breast cancer molecular subtypes. *Breast cancer research: BCR* 12, R77 (2010).
54. Hill, V. K. et al. Genome-wide DNA methylation profiling of CpG islands in breast cancer identifies novel genes associated with tumorigenicity. *Cancer research* 71, 2988-2999 (2011).
55. Meissner, A. et al. Genome-scale DNA methylation maps of pluripotent and differentiated cells. *Nature* 454, 766-770 (2008).
56. Consortium, E. P. An integrated encyclopedia of DNA elements in the human genome. *Nature* 489, 57-74 (2012).
57. Lizardi, P. M. et al. Mutation detection and single-molecule counting using isothermal rolling-circle amplification. *Nature genetics* 19, 225-232 (1998).
58. Schweitzer, B. et al. Immunoassays with rolling circle DNA amplification: a versatile platform for ultrasensitive antigen detection. *Proceedings of the National Academy of Sciences of the United States of America* 97, 10113-10119 (2000).
59. Schweitzer, B. & Kingsmore, S. Combining nucleic acid amplification and detection. *Current opinion in biotechnology* 12, 21-27 (2001).

The invention claimed is:

1. A method of detecting a nucleic acid, said method including the step of combining an isolated nucleic acid and a paramagnetic particle, the paramagnetic particle having a coating that comprises one or more chemical moieties to reversibly bind the isolated nucleic acid, wherein the isolated nucleic acid and the particle are capable of forming a complex which can be detected by visual inspection, wherein the complex is formed by flocculation of the particle by the nucleic acid in a flocculation buffer at a pH below 7 and wherein flocculation is reversible by increasing the pH.

2. The method of claim 1, wherein the presence or relative amount of nucleic acid is indicated by absent or relatively reduced flocculation compared to the flocculation observed in the absence of, or at a relatively lower amount or concentration of, the nucleic acid.

3. The method of claim 1, wherein the paramagnetic particle is an SPRI particle.

4. The method of claim 1, wherein the flocculation buffer is at a pH of (i) about pH 3.6-5.5; or (ii) about pH 4.4.

5. The method of claim 1, wherein the flocculation buffer pH is titrated post flocculation for semi-quantification.

6. The method of claim 1, which further comprises a coloring agent to facilitate, assist or enhance visual detection of the nucleic acid:particle complex.

7. The method of claim 1, wherein the nucleic acid is an amplification product produced by nucleic acid sequence amplification of a target nucleic acid.

8. The method of claim 7, wherein nucleic acid sequence amplification is by polymerase chain reaction (PCR).

9. The method of claim 7, wherein nucleic acid sequence amplification is by isothermal nucleic acid sequence amplification.

10. The method of claim 9, wherein isothermal nucleic acid sequence amplification is recombinase polymerase amplification (RPA) or rolling circle amplification (RCA).

11. The method of claim 7, wherein the amplification product is amplified from a target nucleic acid that has been obtained by the sequential steps of: (a) gravity filtration of a nucleic acid sample that comprises the target nucleic acid;

(b) binding of the target nucleic acid to a particle; and (c) elution of the target nucleic acid from the particle.

12. The method of claim 11, wherein the volume of target nucleic acid at step (b) and at step (c) is about 5-10 µL.

13. The method of claim 1 for detecting a pathogenic or non-pathogenic organism.

14. The method of claim 13, wherein the pathogenic organism is a plant pathogen.

15. The method of claim 13, wherein the pathogenic organism is a human or other animal pathogen.

16. The method of claim 1, which is for detecting one or more biomarkers associated with a disease or condition.

17. The method of claim 16, wherein the one or more biomarkers comprises tumour antigens or markers and/or tumour suppressor genes.

18. The method of claim 16, wherein the one or more biomarkers include nucleotide sequence polymorphisms.

19. The method of claim 18, wherein the one or more biomarkers include one or somatic mutations and/or single nucleotide polymorphisms (SNPs).

20. The method of claim 16, wherein the one or more biomarkers are, or are associated with epigenetic events.

21. The method of claim 20, wherein the epigenetic events include DNA methylation and/or DNA hydroxymethylation events.

22. The method of claim 16, wherein the disease or condition includes cancers, tumours, lymphomas, leukemias and other malignancies, infectious diseases, inflammatory diseases, autoimmune diseases, respiratory diseases, gastrointestinal diseases, neural diseases, diseases of the reproductive system and/or psychiatric conditions.

23. The method of claim 1, wherein the method is used to detect the nucleic acid in an environmental sample or source.

24. The method of claim 23, wherein the environmental sample or source is water, air and/or a soil sample.

25. The method of claim 24, wherein the water sample is waste water and/or effluent.

26. The method of claim 1, for detecting the nucleic acid in a food, beverage or other consumable sample.

27. The method of claim 1, wherein the one or more chemical moieties are or comprise carboxyl-containing moieties.

* * * * *

SEQUENCE LISTING

<160> NUMBER OF SEQ ID NOS: 29

<210> SEQ ID NO 1
<211> LENGTH: 33
<212> TYPE: DNA
<213> ORGANISM: Artificial sequence
<220> FEATURE:
<223> OTHER INFORMATION: PCR primer

<400> SEQUENCE: 1
gctcttgatt taggtacaac tctttccctc gtc                                33

<210> SEQ ID NO 2
<211> LENGTH: 33
<212> TYPE: DNA
<213> ORGANISM: Artificial sequence
<220> FEATURE:
<223> OTHER INFORMATION: PCR primer

<400> SEQUENCE: 2
atatatctgt ataggaatcc cactgaattt ttc                                33

<210> SEQ ID NO 3
<211> LENGTH: 33
<212> TYPE: DNA
<213> ORGANISM: Artificial sequence
<220> FEATURE:
<223> OTHER INFORMATION: PCR primer

<400> SEQUENCE: 3
tttccacagg gtttgtgtac gagattggta ttc                                33

<210> SEQ ID NO 4
<211> LENGTH: 33
<212> TYPE: DNA
<213> ORGANISM: Artificial sequence
<220> FEATURE:
<223> OTHER INFORMATION: PCR primer

<400> SEQUENCE: 4
ttctccggtg tccgttcgca ctgtagacaa tcg                                33

<210> SEQ ID NO 5
<211> LENGTH: 33
<212> TYPE: DNA
<213> ORGANISM: Artificial sequence
<220> FEATURE:
<223> OTHER INFORMATION: PCR primer

<400> SEQUENCE: 5
tttgtccgaa acgacgtaca gccatttaac ctt                                33

<210> SEQ ID NO 6
<211> LENGTH: 32
<212> TYPE: DNA
<213> ORGANISM: Artificial sequence
<220> FEATURE:
<223> OTHER INFORMATION: PCR primer

<400> SEQUENCE: 6
ttctacgtcg gggtatttac tagctggaaa ag        32

<210> SEQ ID NO 7
<211> LENGTH: 33
<212> TYPE: DNA
<213> ORGANISM: Artificial sequence
<220> FEATURE:
<223> OTHER INFORMATION: PCR primer

<400> SEQUENCE: 7
attgaaggac tcatacaagg ttgcatcaaa ata        33

<210> SEQ ID NO 8
<211> LENGTH: 33
<212> TYPE: DNA
<213> ORGANISM: Artificial sequence
<220> FEATURE:
<223> OTHER INFORMATION: PCR primer

<400> SEQUENCE: 8
tttccttttg caactcctac agagtgtcta taa        33

<210> SEQ ID NO 9
<211> LENGTH: 30
<212> TYPE: DNA
<213> ORGANISM: Artificial sequence
<220> FEATURE:
<223> OTHER INFORMATION: PCR primer

<400> SEQUENCE: 9
agttaatcct ttgccgaaat ttgattctac        30

<210> SEQ ID NO 10
<211> LENGTH: 30
<212> TYPE: DNA
<213> ORGANISM: Artificial sequence
<220> FEATURE:
<223> OTHER INFORMATION: PCR primer

<400> SEQUENCE: 10
gtgctcgatg tcaacatgaa gtactagctc        30

<210> SEQ ID NO 11
<211> LENGTH: 33
<212> TYPE: DNA
<213> ORGANISM: Artificial sequence
<220> FEATURE:
<223> OTHER INFORMATION: PCR primer

<400> SEQUENCE: 11
ggaagatctg ctcatgctcg cggccgccat gcc        33

<210> SEQ ID NO 12
<211> LENGTH: 33
<212> TYPE: DNA
<213> ORGANISM: Artificial sequence
<220> FEATURE:

<223> OTHER INFORMATION: PCR primer

<400> SEQUENCE: 12
gagcgcgtaa gcattgcgca cagcgaccag aaa       33

<210> SEQ ID NO 13
<211> LENGTH: 33
<212> TYPE: DNA
<213> ORGANISM: Artificial sequence
<220> FEATURE:
<223> OTHER INFORMATION: PCR primer

<400> SEQUENCE: 13
aagtggcgcg aggcggacga aatgctgcga gac       33

<210> SEQ ID NO 14
<211> LENGTH: 33
<212> TYPE: DNA
<213> ORGANISM: Artificial sequence
<220> FEATURE:
<223> OTHER INFORMATION: PCR primer

<400> SEQUENCE: 14
acgtgcgtgc cgttgtagcg ctcgcggtag acg       33

<210> SEQ ID NO 15
<211> LENGTH: 31
<212> TYPE: DNA
<213> ORGANISM: Artificial sequence
<220> FEATURE:
<223> OTHER INFORMATION: PCR primer

<400> SEQUENCE: 15
ctgtgacgca cagttcatag agataacctt c       31

<210> SEQ ID NO 16
<211> LENGTH: 33
<212> TYPE: DNA
<213> ORGANISM: Artificial sequence
<220> FEATURE:
<223> OTHER INFORMATION: PCR primer

<400> SEQUENCE: 16
aaaagcagtc ttacttccat gatttcttta act       33

<210> SEQ ID NO 17
<211> LENGTH: 32
<212> TYPE: DNA
<213> ORGANISM: Artificial sequence
<220> FEATURE:
<223> OTHER INFORMATION: PCR primer

<400> SEQUENCE: 17
aaattaacaa ttcacaagc ttaatacact cc       32

<210> SEQ ID NO 18
<211> LENGTH: 33
<212> TYPE: DNA
<213> ORGANISM: Artificial sequence
<220> FEATURE:
<223> OTHER INFORMATION: PCR primer

<400> SEQUENCE: 18
tatagaaagt acagcaaaaa ctattcttaa acc       33

```
<210> SEQ ID NO 19
<211> LENGTH: 33
<212> TYPE: DNA
<213> ORGANISM: Artificial sequence
<220> FEATURE:
<223> OTHER INFORMATION: PCR primer

<400> SEQUENCE: 19
ttgaaggaag taagaaaaca attgatcaaa ata                                    33

<210> SEQ ID NO 20
<211> LENGTH: 33
<212> TYPE: DNA
<213> ORGANISM: Artificial sequence
<220> FEATURE:
<223> OTHER INFORMATION: PCR primer

<400> SEQUENCE: 20
ctaaaacgct tattaaatta tgtgcttctt cta                                    33

<210> SEQ ID NO 21
<211> LENGTH: 33
<212> TYPE: DNA
<213> ORGANISM: Artificial sequence
<220> FEATURE:
<223> OTHER INFORMATION: PCR primer

<400> SEQUENCE: 21
attttggcga ggaaggtaaa gagagaaagt agt                                    33

<210> SEQ ID NO 22
<211> LENGTH: 32
<212> TYPE: DNA
<213> ORGANISM: Artificial sequence
<220> FEATURE:
<223> OTHER INFORMATION: PCR primer

<400> SEQUENCE: 22
gagttcctgc ttctgcttat tggctgcttc tt                                     32

<210> SEQ ID NO 23
<211> LENGTH: 32
<212> TYPE: DNA
<213> ORGANISM: Artificial sequence
<220> FEATURE:
<223> OTHER INFORMATION: PCR primer

<400> SEQUENCE: 23
caatccaggg aaatgtcacg tccattcatt cc                                     32

<210> SEQ ID NO 24
<211> LENGTH: 31
<212> TYPE: DNA
<213> ORGANISM: Artificial sequence
<220> FEATURE:
<223> OTHER INFORMATION: PCR primer

<400> SEQUENCE: 24
cctatgcgaa catcccagtg acgttgcctt c                                      31

<210> SEQ ID NO 25
<211> LENGTH: 31
<212> TYPE: DNA
<213> ORGANISM: Artificial sequence
<220> FEATURE:
<223> OTHER INFORMATION: RPA/PCR primer
```

```
<400> SEQUENCE: 25
cctggagcgc ggcaggaagc cttatcagtt g                                   31

<210> SEQ ID NO 26
<211> LENGTH: 30
<212> TYPE: DNA
<213> ORGANISM: Artificial sequence
<220> FEATURE:
<223> OTHER INFORMATION: RT-RPA primer

<400> SEQUENCE: 26
gctagggtta cattccattt tgatggtgac                                     30

<210> SEQ ID NO 27
<211> LENGTH: 30
<212> TYPE: DNA
<213> ORGANISM: Artificial sequence
<220> FEATURE:
<223> OTHER INFORMATION: RT-PCR primer

<400> SEQUENCE: 27
tcctgctgag ggacgcgtgg gctcatcttg                                     30

<210> SEQ ID NO 28
<211> LENGTH: 64
<212> TYPE: DNA
<213> ORGANISM: Artificial sequence
<220> FEATURE:
<223> OTHER INFORMATION: Circular probe

<400> SEQUENCE: 28
tggtcttaaa aactctttcg ttgtcattgg gataggcgat tctaaatttc tcaacgaaat    60
ctgg                                                                 64

<210> SEQ ID NO 29
<211> LENGTH: 47
<212> TYPE: DNA
<213> ORGANISM: Artificial sequence
<220> FEATURE:
<223> OTHER INFORMATION: RT-PCR amplicon

<400> SEQUENCE: 29
cctggagcgc ggcaggaagc cttatcagtt gtgagtagga ccagtcg                  47
```